United States Patent
Sheng et al.

(10) Patent No.: US 12,103,925 B2
(45) Date of Patent: Oct. 1, 2024

(54) CRYSTAL AND AMORPHOUS FORM OF TOLEBRUTINIB, PREPARATION METHOD THEREFOR, AND USE THEREOF

(71) Applicant: HANGZHOU SOLIPHARMA CO., LTD., Zhejiang (CN)

(72) Inventors: Xiaohong Sheng, Zhejiang (CN); Xiaoxia Sheng, Zhejiang (CN); Yu Dai, Zhejiang (CN)

(73) Assignee: HANGZHOU SOLIPHARMA CO., LTD., Hangzhou (CN)

( * ) Notice: Subject to any disclaimer, the term of this patent is extended or adjusted under 35 U.S.C. 154(b) by 52 days.

(21) Appl. No.: 18/475,489

(22) Filed: Sep. 27, 2023

(65) Prior Publication Data

US 2024/0018142 A1    Jan. 18, 2024

Related U.S. Application Data

(63) Continuation of application No. PCT/CN2022/088495, filed on Apr. 22, 2022.

(30) Foreign Application Priority Data

Apr. 23, 2021 (CN) .................. 202110440752.X
Apr. 30, 2021 (CN) .................. 202110479686.7

(51) Int. Cl.
C07D 471/04 (2006.01)
A61K 31/437 (2006.01)

(52) U.S. Cl.
CPC ........ *C07D 471/04* (2013.01); *C07B 2200/13* (2013.01)

(58) Field of Classification Search
CPC ..... C07D 471/04; A61K 31/437; A61P 25/00; A61P 29/00; A61P 35/00; A61P 37/00
USPC ........................................... 546/118; 514/303
See application file for complete search history.

(56) References Cited

U.S. PATENT DOCUMENTS

2021/0244720 A1* 8/2021 Cho et al. .......... A61K 31/4545
                                                    514/303

FOREIGN PATENT DOCUMENTS

| CN | 106459049 A | 2/2017 |
|---|---|---|
| WO | WO-2017/041536 A1 | 3/2017 |
| WO | WO-2021/150476 A1 | 7/2021 |
| WO | WO-2022/121670 A1 | 6/2022 |

OTHER PUBLICATIONS

International Search Report dated Jul. 20, 2022 issued in International Application No. PCT/CN2022/088495, with English translation, 8 pages.

* cited by examiner

*Primary Examiner* — Charanjit Aulakh
(74) *Attorney, Agent, or Firm* — FOLEY & LARDNER LLP

(57) ABSTRACT

The present application provides a crystalline form of tolebrutinib, an amorphous form, and a method of preparation thereof and a use thereof, and the crystalline form of tolebrutinib provided in the present application has at least one of the following advantages: good stability, low moisture attraction, uniform particle size distribution, solubility meeting the requirements for medicinal use, stable storage, avoiding phase transformation of the drug in the process of development and in storage, and a reliable method for the preparation thereof, which has a great development value. The amorphous form of tolebrutinib provided in this application, while possessing better solubility than that of tolebrutinib in the crystalline state, still possesses good stability of placement and acceptable hygroscopicity, and has high medicinal value.

24 Claims, 16 Drawing Sheets

CRYSTAL AND AMORPHOUS FORM OF TOLEBRUTINIB, PREPARATION METHOD THEREFOR, AND USE THEREOF

CROSS-REFERENCE TO RELATED APPLICATIONS

This application claims all the benefits of the Chinese patent application No. 202110440752.X filed on Apr. 23, 2021 with the China National Intellectual Property Administration of the People's Republic of China, and the Chinese patent application No. 202110479686.7 filed on Apr. 30, 2021 with the China National Intellectual Property Administration of the People's Republic of China, of which the entire contents are incorporated herein by reference.

TECHNICAL FIELD

The present application relates to the field of medicinal chemistry. In particular, the present application relates to a crystal and an amorphous form of tolebrutinib, preparation method therefor, and use thereof.

BACKGROUND

Polymorph or polymorphism is a particular property of certain molecule and molecular composition. Different crystalline forms of certain compounds arise from different molecular packing in the crystal lattice, and these crystalline forms have different crystal structures and physical properties, such as solubility, stability, thermal property, mechanical property, purification capability, X-ray diffraction pattern, infrared absorption spectroscopy, Raman spectroscopy, solid state nuclear magnetic resonance, etc.

It is found that novel crystal forms of pharmaceutically active ingredients (including anhydrates, hydrates, and solvates) may produce more workable advantages or provide materials having better physical and chemical characteristics, e.g., better bioavailability, better storage stability, better processibility, and easiness to be purified, or as an intermediate crystal form that can be easily converted into other crystal forms. Some specific crystal forms of active pharmaceutical ingredients also can help medicines to improve their properties. Thus, the novel crystal forms of active pharmaceutical ingredients expand the selection of feasible forms in the pharmaceutics, e.g., improved dissolution, improved shelf life, and improved processibility.

Tolebrutinib (development code SAR442168), initially developed by Principia and later acquired by Sanofi, has been integrated into Sanofi's product line. Tolebrutinib, a BTK inhibitor, is used in the treatment of various conditions including cancer, autoimmune diseases such as multiple sclerosis and Myasthenia gravis, inflammatory diseases and thromboembolic diseases. Its structural formula is as follows:

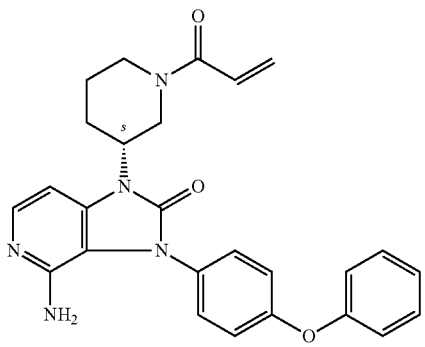 [SMILES: C=CC(=O)N1CCC[C@@H](n2c(=O)n(-c3ccc(Oc4ccccc4)cc3)c3c(N)nccc32)C1]

However, so far there is no relevant disclosure on the crystal form of this compound in the prior art. Therefore, it is necessary to conduct a comprehensive and systematic polymorphic screening of tolebrutinib and select crystalline forms with beneficial properties for product development of tolebrutinib.

The inventors have surprisingly discovered two crystal forms of tolebrutinib during research. The crystal forms of tolebrutinib as provided in this application have at least one of the following advantages: good stability, low moisture absorption, uniform particle size, and a solubility meets pharmaceutical requirements, capability for stable storage, prevention of polymorphic transformation during development and storage, reliable preparation method, and significant developmental value.

Additionally, the inventors of this applicant have pleasantly discovered an amorphous form of tolebrutinib. As is well known, solid powders can exist in two physical states: amorphous and crystalline. Typically, amorphous solids exhibit lower stability and higher hygroscopicity, which can limit their pharmaceutical value. However, the amorphous form of tolebrutinib discovered by the applicant not only possesses better solubility than crystalline tolebrutinib, but also maintains good storage stability and acceptable hygroscopicity. This discovery adds significant pharmaceutical value to tolebrutinib.

SUMMARY OF THE INVENTION

In response to the deficiencies in the prior art, the objective of the application is to provide a crystal and an amorphous form of tolebrutinib, preparation method therefor, and use thereof.

One object of the present application is to provide Form 1 of tolebrutinib (hereinafter referred to as Form 1), wherein the X-ray powder diffraction (XRPD) pattern comprises at least four characteristics peaks at 2θ values of 10.4°±0.2°, 11.4°±0.2°, 20.6°±0.2°, 16.7°±0.2° and 22.7°±0.2°.

Furthermore, the XRPD pattern of Form 1 also comprises one or two or more characteristics peaks at 2θ values of 4.2°±0.2°, 15.8°±0.2°, 17.9°±0.2°, 20.8°±0.2° and 24.8°±0.2°, or/and wherein the XRPD pattern of Form 1 also comprise one or two or more characteristics peaks at 2θ values of 10.9°±0.2°, 21.3°±0.2°, 23.5±0.2°, 25.3±0.2° and 25.7±0.2°.

Furthermore, the XRPD pattern of Form 1 comprise characteristic peaks at the following 2θ values:

| 2θ ± 0.2° |
| --- |
| 4.2 |
| 10.4 |
| 10.9 |
| 11.4 |
| 15.8 |
| 16.7 |
| 17.9 |
| 20.3 |
| 20.6 |
| 20.8 |
| 21.0 |
| 21.3 |
| 22.7 |
| 23.5 |
| 23.7 |
| 24.8 |
| 25.3 |
| 25.7 |
| 26.9 |
| 27.2 |
| 27.4 |
| 31.1 |
| 35.5 |

In a preferred embodiment of the present application, the XRPD pattern of Form 1 is substantially as depicted in FIG. 7.

In a preferred embodiment of the present application, the TGA thermogram of Form 1 is substantially as depicted in FIG. 8.

In a preferred embodiment of the present application, the DSC thermogram of Form 1 begins to show an endothermic peak at about 126° C.

In a preferred embodiment of the present application, the DSC thermogram of Form 1 is substantially as depicted in FIG. 9.

In a preferred embodiment of the present application, the Fourier transform infrared (FT-IR) spectrum of Form 1 comprises at least one band at wave numbers of 840.7±2 cm-1, 978.3±2 cm-1, 1472.3±2 cm-1 and 1492.5±2 cm-1.

Preferably, the FT-IR spectrum of Form 1 further comprise at least one or two or more bands at wave numbers of 748.5±2 cm-1, 1230.6±2 cm-1, 1396.8±2 cm-1, 14447.4±2 cm-1, 1508.9±2 cm-1, 1588.1±2 cm-1, 1638.1±2 cm-1 and 1698.4±2 cm-1.

In a preferred embodiment of the present application, the FT-IR spectrum of Form 1 is substantially as depicted in FIG. 13.

In a preferred embodiment of the present application, Form 1 is anhydrous.

One of the objects of the present application is also to provide a preparation method of tolebrutinib Form 1, wherein the method is selected from any one of the following methods:

1) Dissolving tolebrutinib in solvent 1 to form a solution, volatilizing, recrystallizing, separating, and drying to obtain Form 1.

Wherein, the solvent 1 is acetone.

Preferably, the dissolving step is performed at room temperature.

Preferably, the volatilization is carried out at room temperature.

2) Dissolving tolebrutinib in co-solvent to form a solution, stirring (1), adding anti-solvent, stirring (2), recrystallizing, separating, and drying to obtain Form 1.

Wherein, the co-solvent is selected from ethanol, acetone and tetrahydrofuran, as individual or mixed solvents; the anti-solvent is selected from water, n-heptane and n-hexane as individual or mixed solvents, preferably a water-containing mixed solvent.

The stirring (1) is an optional step.

The stirring (2) is an optional step, particularly applicable to embodiments where solid precipitation doesn't occur immediately after adding the anti-solvent; for cases where solid precipitation occurs immediately after adding the anti-solvent, this step can be omitted.

Preferably, the volume ratio of the anti-solvent to the co-solvent is 0.1:1, more preferably, it is in the range of 1:1 to 8:1.

Preferably, the dissolving step is performed at room temperature.

Preferably, the stirring is performed at a certain temperature, and the certain temperature is ≤30° C.; the stirring time is ≥0.30 min.

3) Dissolving tolebrutinib in solvent 2 to form a suspension, stirring at room temperature, separating, and drying to obtain Form 1.

Wherein, the solvent 2 is selected from either ethanol or ethyl acetate, or a mixture thereof. Preferably, the solvent is ethanol. The mass-volume ratio (mg/mL) of the tolebrutinib and solvent 2 is 20:1-100:1.

Preferably, the mass-to-volume ratio (mg/mL) between tolebrutinib and solvent 2 is in the range of 25:1 to 50:1.

Tolebrutinib Form 1 of the present application has the following beneficial effects:

1) Tolebrutinib Form 1 has good stability, which is beneficial for the storage of samples and the stability of formulations. Form 1 remains unchanged after being stored for 10 months under both long-term and accelerated conditions. The purity of tolebrutinib Form 1 remains essentially unchanged before and after storage. In addition, when tolebrutinib Form 1 is mixed with excipients to create a pharmaceutical formulation, its crystal form remains unchanged for at least 14 days at 25° C./60% RH. This demonstrates that both the active pharmaceutical ingredient of tolebrutinib Form 1 and formulations prepared using the Form 1 of this application exhibit robust stability under rigorous conditions.

2) Tolebrutinib Form 1 has low hygroscopicity, requiring no specific humidity conditions during production and storage environments. This characteristic makes it suitable for industrial scale production and is advantageous for the storage of both the compound and its formulated products.

3) Tolebrutinib Form 1 demonstrates excellent solubility, with a solubility around 20 mg/mL in a medium simulating the physiological pH of the human stomach. This characteristic contributes to achieving optimal drug bioavailability and efficacy, meeting pharmaceutical requirements.

4) Tolebrutinib Form 1 has good compressibility, which is beneficial for formulation process, enhancing product appearance, and improving product quality.

Tolebrutinib Form 1 exhibits a desirable appearance as a finely powdered solid with small particles, contributing to improved flowability.

6) The preparation conditions of tolebrutinib Form 1 are mild, high repeatable, and displaying promising potential for industrial-scale production.

7) Tolebrutinib Form 1 displays a very high chemical purity. The Form 1 samples in this application, without any special purification procedures, have demonstrated a purity of 99.8%, indicating that high purity is an inherent beneficial property of Form 1 crystal form. Even after stability testing, as shown in Table 2, after having been exposed to open conditions for at 40° C./75% RH for 10 months, the purity remains 99.5%. This highlights that Form 1 maintains not only high chemical purity but also remarkable chemical stability.

In conclusion, Tolebrutinib Form 1 has good physicochemical properties, making it easy to formulate into product formulations. This aspect further ensures the quality of both the compound and formulated products, enhancing the effectiveness of tolebrutinib treatment.

Another object of the present application is to provide tolebrutinib Form 2 (hereinafter referred to as Form 2), wherein the XRPD pattern of Form 2 comprises at least four characteristics peaks at 2θ values of 7.8°±0.2°, 12.0°±0.2°, 18.5°±0.2°, 18.8°±0.2 and 22.9°±0.2°.

Furthermore, the XRPD pattern of the Form 2 also comprises one or two or more characteristics peaks at 2θ values of 11.1°±0.2°, 13.7°±0.2°, 16.2±0.2°, 23.9°±0.2° and 24.9°±0.2°, or/and wherein the XRPD pattern of Form 2 also comprises one or two or more characteristics peaks at 2θ values of 13.3°±0.2°, 14.1°±0.2°, 20.3°±0.2° and 21.7°±0.2°.

Further, the XRPD pattern of Form 2 comprises characteristic peaks at the following 2θ values:

| 2θ ± 0.2° |
| --- |
| 7.8 |
| 11.1 |
| 12.0 |
| 13.3 |
| 13.7 |
| 16.2 |
| 18.5 |
| 18.8 |
| 19.3 |
| 20.3 |
| 20.9 |
| 21.5 |
| 21.7 |
| 22.9 |
| 23.9 |
| 24.9 |
| 26.4 |
| 27.9 |
| 29.0 |
| 30.4 |

In a preferred embodiment of the present application, the XRPD pattern of Form 2 is substantially as depicted in FIG. 14.

In a preferred embodiment of the present application, the TGA thermogram of Form 2 is substantially as depicted in FIG. 15.

In a preferred embodiment of the present application, the DSC thermogram of Form 2 begins to show an endothermic peak at about 160-164° C.

In a preferred embodiment of the present application, the DSC thermogram of Form 2 is substantially as depicted in FIG. 6.

In a preferred embodiment of the present application, the FT-IR spectrum of Form 2 comprises bands at wave numbers of 1699±2 cm-1, 1229±2 cm-1, 1486 cm-1 and 1507±2 cm-1.

Preferably, the FT-IR spectrum of Form 2 further comprises at least one or two or more bands at wave numbers of 693±2 cm-1, 1395±2 cm-1, 1507±2 cm-1 and 1626±2 cm-1.

In a preferred embodiment of the present application, the FT-IR spectrum of Form 2 is substantially as depicted in FIG. 19.

In a preferred embodiment of the present application, Form 2 is anhydrous.

One of the objects of the present application is also to provide a preparation method of tolebrutinib Form 2, wherein the method is selected from any one of the following methods:

1) Dispersing tolebrutinib in solvent 3 to form a suspension, stirring at a controlled constant temperature, separating solids, and drying to obtain Form 2;

Wherein, the stirring at a controlled constant temperature is ≥12 hours, preferably 1-5 days; the controlled constant temperature is ≥30° C., preferably 30-80° C., more preferably 40-70° C.

The solvent 3 is selected from methyl tert-butyl ether (MTBE), n-heptane, 2-butanone, water, n-butyl acetate, diisopropyl ether, 2-butyl alcohol, dichloromethane and 1,4-dioxane, as individual or mixed solvents.

Preferably, the solvent 3 is selected from a mixed solvent of 2-butanone and water, and the mixed volume ratio of 2-butanone and water is in the range of 1:1 to 1:10; or, it is selected from a mixed solvent of n-butyl acetate and dichloromethane, and the mixed volume ratio of n-butyl acetate and dichloromethane is in the range of 1:1 to 1:10.

2) Dissolving tolebrutinib in solvent 4 to form a solution, volatilizing under open vial conditions, and drying.

Wherein, the solvent 4 is selected from toluene and methylcyclohexane, as individual or a mixed solvent.

Preferably, the solvent 4 is a mixed solvent of toluene and methylcyclohexane, and the solvent ratio of toluene and methylcyclohexane is in the range of 5:1 to 1:2.

3) Placing tolebrutinib in a sealed container containing solvent 5 for a minimum of 1 day and followed by drying to obtain Form 2.

Wherein, the solvent 5 is acetonitrile.

Tolebrutinib Form 2 of the present application has the following beneficial effects:

1) The tolebrutinib Form 2 has a high melting point, making it very beneficial to high temperature processes such as hot melt extrusion.

2) The hygroscopicity of tolebrutinib Form 2 is very low, with only 0.3% absorption within the range of 0% RH to 80% RH. This characteristic makes it even more suitable for industrial scale production and storage.

3) Tolebrutinib Form 2 has good physical and chemical stability, contributing to the storage of samples and the stability of formulations. Form 2 remains unchanged for 10 months under both long-term and accelerated conditions. The chemical purity of tolebrutinib Form 2 remains essentially unchanged before and after storage. In addition, when tolebrutinib Form 2 is mixed with excipients to create a pharmaceutical formulation, its crystal form remains unchanged for at least 14 days at 25° C./60% RH. This demonstrates that both the active pharmaceutical ingredient of tolebrutinib Form 1 and formulations prepared using the Form 1 of this application exhibit robust stability under rigorous conditions.

4) Competitive slurry experiments reveal that Tolebrutinib Form 2 is the thermodynamically stable form at temperatures of 30° C. and above.

5) Tolebrutinib Form 2 has good solubility, which is beneficial to achieve optimal drug bioavailability and efficacy, meeting pharmaceutical requirements.

6) Tolebrutinib Form 2 has good compressibility, which is beneficial for formulation process, enhancing product appearance, and improving product quality.

7) Tolebrutinib Form 2 exhibits a desirable appearance as a finely powdered solid with small particles, contributing to improved flowability.

8) The preparation conditions of tolebrutinib Form 2 are mild, highly repeatable, and displaying promising potential for industrial scale production.

Another object of the present application is to provide an amorphous form of tolebrutinib, wherein the XRPD pattern of the amorphous form comprises no diffraction peaks in the range of 3° to 40° 2θ values.

Preferably, the XRPD pattern of the amorphous form of tolebrutinib has/comprises a broad hump in the range of 10°-40° at 2θ values.

In a preferred embodiment of the present application, the XRPD pattern of the amorphous form of tolebrutinib is substantially as depicted in FIG. 1.

In a preferred embodiment of the present application, the TGA thermogram of the amorphous form of tolebrutinib is substantially as depicted in FIG. 2.

In a preferred embodiment of the present application, the DSC thermogram of the amorphous form of tolebrutinib is substantially as depicted in FIG. 3.

In a preferred embodiment of the present application, the FT-IR spectrum of the amorphous form of tolebrutinib comprises bands at wave numbers of 1703±2 cm-1, 1440±2 cm-1, 788 cm-1 and 753±2 cm-1.

In a preferred embodiment of the present application, the FT-IR spectrum of the amorphous form of tolebrutinib further comprises at least one or two or more bands at wave numbers of 693±2 cm-1, 950±2 cm-1, 1227±2 cm-1, 1391±2 cm-1, 1487±2 cm-1, 1487±2 cm-1, 1588±2 cm-1 and 1625±2 cm-1.

In a preferred embodiment of the present application, the FT-IR spectrum of the amorphous form of tolebrutinib is substantially as depicted in FIG. 6.

One of the objects of the present application is also to provide a preparation method of the amorphous form of tolebrutinib, wherein the method is selected from any one of the following methods:

1) Dissolving tolebrutinib in a co-solvent, then adding anti-solvent, stirring, precipitating solids, separating, and drying.

Wherein, the co-solvent is either DMSO (dimethyl sulfoxide) or toluene, or their mixture; the anti-solvent is selected from water and an ether or their mixture.

Preferably, the co-solvent is DMSO; the anti-solvent is water.

Preferably, the volume ratio of the co-solvent and the anti-solvent is in the range of 10:1 to 1:10, more preferably 1:1.

2) Dissolving tolebrutinib in solvent 6 at high temperature, filtering, stirring at low temperature, separating and drying.

Wherein, the solvent 6 is selected from one or more of the following mixed solvents: trifluoroethanol/water, isopropyl acetate/water, tetrahydrofuran/water, 1,4-dioxane/water, acetonitrile/water and chloroform/water.

Preferably, the solvent 6 is a mixed solvent of trifluoroethanol/water.

Preferably, the high temperature is in the range of 40° C. to 80° C.

Preferably, the low temperature is no more than 10° C.

Surprisingly, the amorphous form of tolebrutinib of the present application has the following unexpected combined beneficial effects:

1) The amorphous form of tolebrutinib of this application has good stability, which is beneficial to the storage of samples and the stability of formulations. The amorphous form of tolebrutinib of this application remains unchanged for 10 months under both long-term and accelerated conditions for 10 months, and its chemical purity remains essentially unchanged before and after storage. The amorphous form of tolebrutinib remains unchanged for 14 days under light and oxidation conditions, respectively, with no essential change observed in its chemical purity before and after storage. In addition, when the amorphous form of tolebrutinib of this application is mixed with excipients to create a pharmaceutical formulation, its amorphous status remains unchanged during a 14-day period at 25° C./60% RH. This demonstrates that both the active pharmaceutical ingredient of amorphous tolebrutinib of this application and formulations prepared using the amorphous form of tolebrutinib of this application exhibit robust stability under rigorous conditions.

2) The amorphous form of tolebrutinib of the present application displays a high chemical purity of ≥98.9%. Moreover, even after 10 months of open storage under long-term conditions, its purity remains unchanged, and it still maintains a purity of 98.0% after 10 months of open storage under accelerated conditions.

3) The amorphous form of tolebrutinib of this application demonstrates excellent solubility, surpassing that of Tolebrutinib Form 1 and Form 2 of the present application. This characteristic is advantageous for achieving optimal drug bioavailability and efficacy, meeting pharmaceutical requirements.

4) The amorphous form of tolebrutinib of the present application has low hygroscopicity, with only a weight gain of about 1.9% within the range of 20% RH to 80% RH, making it suitable for industrial scale production.

5) The amorphous form of tolebrutinib of the present application has good compressibility, which is beneficial for formulation process, enhancing product appearance, and improving product quality.

6) Another object of the present application is also to provide a pharmaceutical composition of tolebrutinib, wherein the composition comprising one or more of tolebrutinib Form 1, or tolebrutinib Form 2, or the amorphous form of tolebrutinib, or any combination thereof, along with at least one pharmaceutically acceptable carrier.

Another object of the present application is also to provide a formulation prepared from the above-mentioned tolebrutinib pharmaceutical composition, wherein the formulation can take various dosage forms including, but are not limited to oral solid dosage forms, topical formulations, and injectable formulations.

In a preferred embodiment of the present application, the formulation/dosage form is selected from tablets, capsules, pills, suppositories, granules, fine granules, powders sustained-release formulations, immediate-release formulations, solutions, suspensions, elixirs, aerosols, etc.

In a preferred embodiment of the present application, the formulation/dosage form is a tablet.

The pharmaceutically acceptable carriers are commonly used excipients in the field, including but not limited to binders, adhesives, surfactants, diluents, anti-adherents, hydrophilic or hydrophobic polymers, and stabilizers, disintegrants, antioxidants, defoaming agents, fillers, glidants/lubricants, adsorbents, preservatives, plasticizers, sweeteners, and any two or more of these carriers.

In the preferred embodiment of the present application, when the formulation is an oral solid dosage form, the filler or diluent is selected from lactose, microcrystalline cellulose, starch, pregelatinized starch, calcium sulfate, calcium hydrogen phosphate, and calcium carbonate, or any combination thereof; the disintegrant is selected from sodium carboxymethyl starch, croscarmellose sodium, low-substituted hydroxypropyl cellulose, and polyvinylpyrrolidone, or any combination thereof; the lubricant/glidant is selected from magnesium stearate, talc, and micropower silica gel, or any combination thereof.

Furthermore, the pharmaceutical composition may also comprise one or more pH adjusting agents or buffers. For example, acids such as acetic acid, boric acid, citric acid, fumaric acid, maleic acid, tartaric acid, malic acid, lactic acid, phosphoric acid and hydrochloric acid, or any combination thereof; or bases, such as sodium hydroxide, sodium phosphate, sodium borate, sodium citrate, sodium acetate, sodium lactate, tris or any combination thereof; Or buffers such as citrate/glucose, sodium bicarbonate, ammonium chloride, or a like. Such buffers, when used as a base, may have counterions other than sodium, such as potassium, magnesium, calcium, ammonium, and other counterions; and the necessary amount of such acids, bases, and buffers to maintain the pH of the components within an acceptable range can be present in the form of a solution or solid.

One of the objects of the present application is also to provide one or more of Form 1, Form 2, and amorphous form of tolebrutinib, or any combination thereof, or the pharmaceutical composition thereof, for use in the preparation of drugs for the treatment of BTK mediated diseases.

One of the objects of the present application is also to provide one or more of Form 1, Form 2, and the amorphous form of tolebrutinib, or the pharmaceutical composition thereof, for use in the preparation of drugs for the treatment of cancer, autoimmune diseases, inflammatory diseases, and thromboembolic diseases.

One of the objects of the present application is also to provide a method for treating BTK mediated diseases, comprising administering to a patient an effective amount of one or more of tolebrutinib Form 1, tolebrutinib Form 2, or the amorphous form of tolebrutinib, or the pharmaceutical composition thereof.

One of the objects of the present application is also to provide a method for the treatment of cancer, autoimmune disease, inflammatory disease and thromboembolic disease using tolebrutinib and its pharmaceutical composition. The method comprising administering to a patient in need a therapeutically effective amount of one or more of tolebrutinib Form 1, tolebrutinib Form 2, and the amorphous form of tolebrutinib of the present application, or any combination thereof, or the pharmaceutical composition thereof.

Preferably, the effective amount of one or more of tolebrutinib Form 1, tolebrutinib Form 2, and the amorphous form of tolebrutinib of the present application is in the range of 0.001 to 10 mg/kg, preferably in the range of 0.005 to 5 mg/kg.

Preferably, the method can be administered once a day, twice a day, three or more times a day. The single dose can range 0.1 mg to 500 mg/kg/day, and the specific dose will be determined based on the actual situation of the patient.

Preferably, the method is administered once a day, with a single oral dose of 10, 30, 60, 90, 120, 150, 180, 210, 300, 450, or 500 mg of one or more of tolebrutinib Form 1, tolebrutinib Form 2, and the amorphous form of tolebrutinib; more preferably 60 or 120 mg.

In the preferred embodiment of the present application, the diseases include but are not limited to acute necrotizing hemorrhagic leukoencephalitis, acute disseminated encephalomyelitis, Addison's disease, agammaglobulinemia, alopecia areata, alopecia universal's, amyloidosis, ankylosing spondylitis, anti-GBM/Anti-TBM nephritis, antiphospholipid syndrome (APS), antiphospholipid antibody syndrome, aplastic anemia, arthritis, autoimmune angioedema, autoimmune dysautonomia, autoimmune hepatitis, autoimmune hyperlipidemia, autoimmune immunodeficiency, autoimmune inner ear disease (AIED), autoimmune myocarditis, autoimmune oophoritis, autoimmune pancreatitis, autoimmune retinopathy, autoimmune thrombocytopenic purpura (ATP), autoimmune thyroid disease, autoimmune urticaria, autoimmune hemolytic anemia, axonal & neuronal neuropathies, Balo disease, Behcet's disease, bullous pemphigoid, cardiomyopathy, Castleman disease, celiac disease, Chagas disease, chronic fatigue syndrome, chronic inflammatory demyelinating polyneuropathy (CIDP), chronic recurrent multifocal ostomyelitis (CRMO), Churg-Strauss syndrome, cicatricial pemphigoid/benign mucosal pemphigoid, coeliac disease, Cogans syndrome, cold agglutinin disease, congenital heart block, coxsackie myocarditis, CREST disease, Crohn's disease, demyelinating neuropathies, dermatitis herpetiformis, dermatomyositis, Devic's disease (neuromyelitis optical), diabetes, discoid lupus, Dressier's syndrome, dry eye, dysautonomia, endometriosis, eosinophilic esophagitis, eosinophilic fasciitis, erythema nodosum, essential mixed cryoglobulinemia, Evans syndrome, experimental allergic encephalomyelitis, fibromyalgia, fibrosing alveolitis, giant cell arteritis (temporal arteritis), giant cell myocarditis, glomerulonephritis, Goodpasture's syndrome, granulomatosis with polyangiitis (GPA) (formerly called Wegener's Granulomatosis), Graves' disease, Guillain-Barre syndrome, Hashimoto's thyroiditis, hemolytic anemia, Henoch-Schonlein purpura, herpes gestations, hypogammaglobulinemia, idiopathic pulmonary fibrosis, idiopathic thrombocytopenic purpura (ITP), IgA nephropathy, IgG4-related sclerosing disease, immunoregulatory lipoproteins, inclusion body myositis, inflammatory bowel disease, interstitial cystitis, juvenile arthritis, juvenile diabetes (Type 1 diabetes), juvenile myositis, Kawasaki syndrome, Lambert-Eaton syndrome, leukocytoclastic vasculitis, lichen planus, lichen sclerosus, ligneous conjunctivitis, linear IgA disease (LAD), lupus (SLE), lupus including lupus nephritis, lyme disease, chronic, Meniere's disease, microscopic polyangiitis, mixed connective tissue disease (MCTD), Mooren's ulcer, Mucha-Habermann disease, mucous membrane pemphigoid, multiple sclerosis, myasthenia gravis, myositis, narcolepsy, neuromyotonia, neutropenia, ocular cicatricial pemphigoid, opsoclonus-myoclonus syndrome, optic neuritis, Ord's thyroiditis, osteoarthritis, palindromic rheumatism, PANDAS (Pediatric Autoimmune Neuropsychiatry Disorders Associated with *Streptococcus*), paraneoplastic cerebellar degeneration, paroxysmal nocturnal hemoglobinuria (PNH), Parry Romberg syndrome, pars planitis (peripheral uveitis), Parsonnage-Turner syndrome, peripheral neuropathy, perivenous encephalomyelitis, pernicious anemia, pemphigus such as pemphigus vulgaris, pemphigus foliaceus, POEMS syndrome, polyarteritis nodosa, polymyalgia rheumatica, polymyositis, postmyocardial infarction syndrome, postpericardiotomy syndrome, primary sclerosing cholangitis, primary biliary cirrhosis, progesterone dermatitis, psoriasis, psoriatic arthritis, psoriaticarthritis, pure red cell aplasia, pyoderma gangrenosum, raynauds phenomenon, reactive arthritis, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm & testicular autoimmunity, stiff person syndrome, Still's disease, subacute bacterial endocarditis (SBE), Susac's syndrome, sympathetic ophthalmia, Takayasu's arteritis, temporal arteritis/Giant cell arteritis, thrombocytopenic purpura (TTP), Tolosa-Hunt syndrome, transverse myelitis, Type I, II, & III autoimmune polyglandular syndromes, ulcerative colitis, undifferentiated connective tissue disease (UCTD), uveitis, vasculitis, vesiculobullous dermatosis, vitiligo, vulvodynia, lupus, or multiple sclerosis (MS).

In the preferred embodiment of the present application, the multiple sclerosis includes but is not limited to relapsing multiple sclerosis (RMS), primary progressive multiple sclerosis (PPMS), secondary progressive multiple sclerosis (SPMS).

One of the objects of the present application is also to provide one or more of tolebrutinib Form 1, tolebrutinib the Form 2, and the amorphous form of tolebrutinib, or pharmaceutical compositions, in combination with other drugs.

The other drugs include, but are not limited to, any one or more of anticancer drugs, corticosteroids, non-corticosteroids, immunosuppressants, anti-inflammatory drugs, and any combination thereof.

Preferably, the other drugs is selected from ibrutinib, acalabrutinib, zanubrutinib, Velexbru and orelabrutinib.

Unless otherwise specified:

The experimental operating temperature generally refers to room temperature, and "room temperature" refers to a temperature between 10° C. and 30° C.

"Stirring" may be carried out by conventional methods in the art. For example, stirring includes magnetic stirring, mechanical stirring, and the like, and the stirring speed is 50-1800 rpm, preferably 300-900 rpm.

"Separation" may be carried out by conventional methods in the art, such as centrifugation or filtration. "Separation" may employ conventional methods in the art, such as centrifugation or filtration. Preferred vacuum filtering, generally at a pressure less than atmospheric pressure for filtration, preferably less than 0.09 MPa.

"Drying" can be carried out by conventional techniques in the art, such as normal temperature drying, blast drying or reduced pressure drying. Reduced pressure or atmospheric pressure may be used. Reduced pressure, preferably with a pressure less than 0.09 MPa. The drying apparatus and method are not limited, and may be a fume hood, a blast oven, a spray dryer, a fluidized bed drying, or a vacuum oven, which may also be carried out under reduced or non-reduced pressure, Reduced pressure, preferably with a pressure less than 0.09 MPa.

Unless otherwise specified, the ratios involved in this application, between solid and liquid, are mass-volume ratios, and between liquids and liquids, are volume ratios.

SPECIFIC IMPLEMENTATIONS

Figure 1:
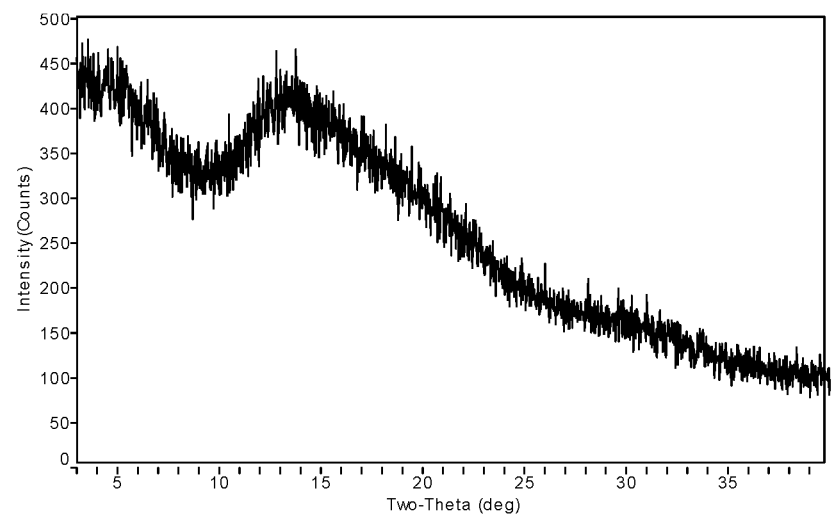
FIG. 1 is an XRPD pattern of the sample of Example 1-1 (the amorphous form of tolebrutinib).

The technical implementations of the present application are described in detail below with reference to the accompanying drawings and embodiments. However, this does not limit the scope of this application to the specific embodiments described.

In this application, X-ray powder diffraction (XRPD) data were collected using a BrukerD8 Advance diffractometer; parameters are as follows: Cu radiation; wavelength: 1.54 Å; Current voltage: 40 KV, 40 mA; Scan range: 3~40'2θ.

In this application, the thermogravimetric analysis (TGA) data were collected using a TA Instruments Q500 TGA; the parameters were as follows: high resolution mode; heating rate: 10° C./min; gas: N2; sample pan: platinum crucible.

In this application, Differential Thermal Analysis (DSC) data were obtained using a TA Instruments Q200 DSC; parameters were as follows: ramp rate: 10° C./min; gas: N2; sample pan: aluminum pan with lid.

In this application, mDSC data were collected using a TA Instruments Q200 DSC; parameters were as follows: amplitude: ±0.048° C., cycle 60 s, heating rate: 2° C./min, gas: N2; sample pan: aluminum pan with lid.

In this application, dynamic moisture adsorption analysis (DVS) data and isothermal adsorption analysis data were obtained using a TA Instruments Q5000 TGA; parameters are as follows: temperature: 25° C.; relative humidity range: 0% RH-80% RH; dm/dt=0.001%/min; equilibration time: gas: N2; sample pan: platinum pan.

In this application, Fourier transform infrared spectroscopy (FT-IR) data were collected using a Bruker Tensor 27; the parameters were as follows: ATR method, collection range 600 cm-1-4000 cm-1, resolution 4 cm-1.

In this application, the polarized light microscope (PLM) images were collected using a XPV~990E polarized light microscope; a small amount of powder sample was placed on a glass slide, a small amount of mineral oil was added dropwise to disperse the sample, a cover glass was placed on the slide, and the sample was placed on the slide. Observing and taking pictures on the stage.

In this application, the HPLC parameters for chemical stability and solubility are as follows:

| High Performance Liquid Chromatography (HPLC): | |
| --- | --- |
| Column | Titank-C18 3um (100*4.6 mm) |
| Column temperature: | 40° C. |
| Flow rate | 1.0 mL/min |
| Wavelength | 254 nm |
| Mobile phase | Mobile phase A: 0.01% TFA in H2O |
| | Mobile phase: 0.01% TFA in ACN |
| Diluent | ACN:H2O = 1:1 (v/v) |

| Gradient | time (min) | A (%) | B (%) |
| --- | --- | --- | --- |
| | 0 | 95 | 5 |
| | 0.5 | 95 | 5 |
| | 8.0 | 5 | 95 |
| | 8.1 | 95 | 5 |
| | 12 | 95 | 5 |

In the following embodiments, experimental methods without specific conditions are conducted using standard procedures and conditions, or as instructed in commercial manuals. Unless otherwise specified, the reagents and materials used in this application are commercially available.

PREPARATION EXAMPLES

Referring to the synthetic route in Example 3 of WO2016196840 A1, the crude product of tolebrutinib was obtained.

The crude products mentioned above can also be obtained through other synthetic routes or procurement.

Example 1-1: Preparation of the Amorphous Form of Tolebrutinib

About 20 mg of the crude product of tolebrutinib was dissolved in 1.0 mL of dimethyl sulfoxide. After adding 1.0 mL of water, solid precipitated. After stirring for two hours, the mixture was centrifugation, and the resulting solids were vacuum dried at room temperature for 24 hours, yielding sample 1-1.

The XRPD pattern of sample 1-1 is shown in FIG. 1.

Figure 2:
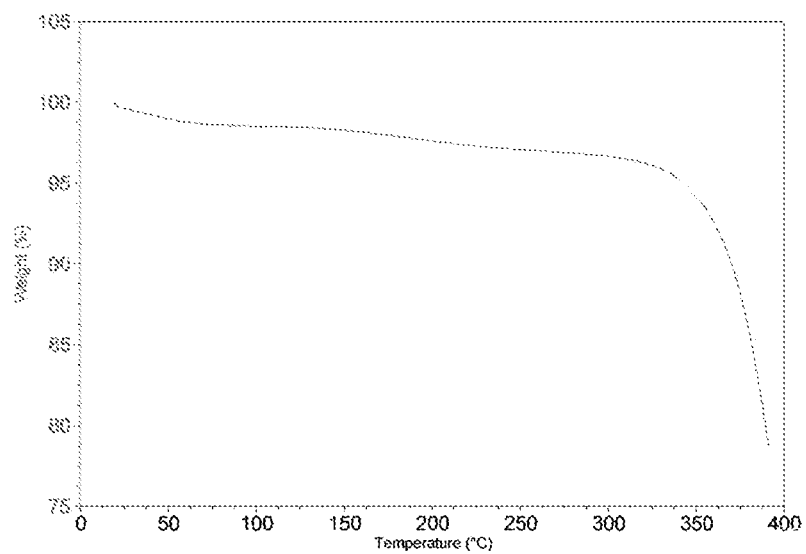
FIG. 2 is a TGA thermogram of the sample of Example 1-1.

The TGA characterization data of samples 1-1 were collected; The weight loss before 100° C. is 1.5%, AND the decomposition temperature is 359° C., as shown in FIG. 2.

Figure 3:
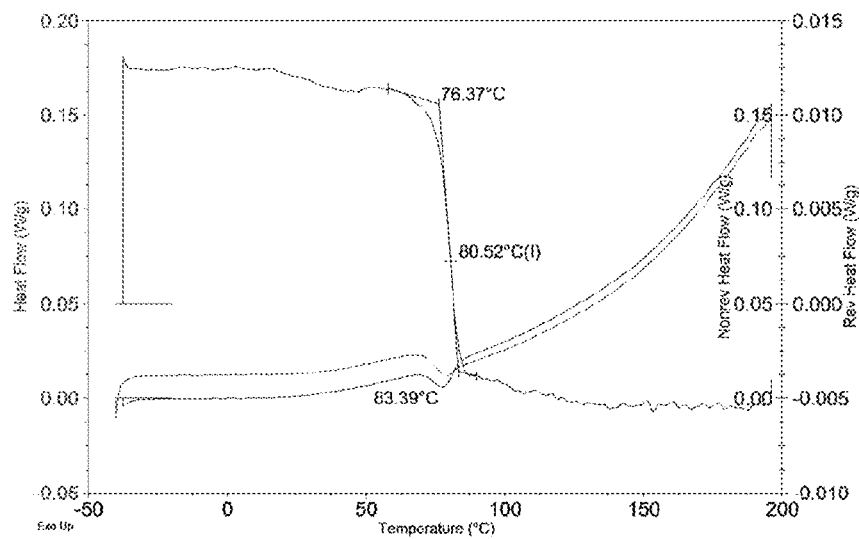
FIG. 3 is an mDSC thermogram of the sample of Example 1-1.

The mDSC of sample 1-1 is shown in FIG. 3, with a Tg of 80.5° C.

Figure 4:
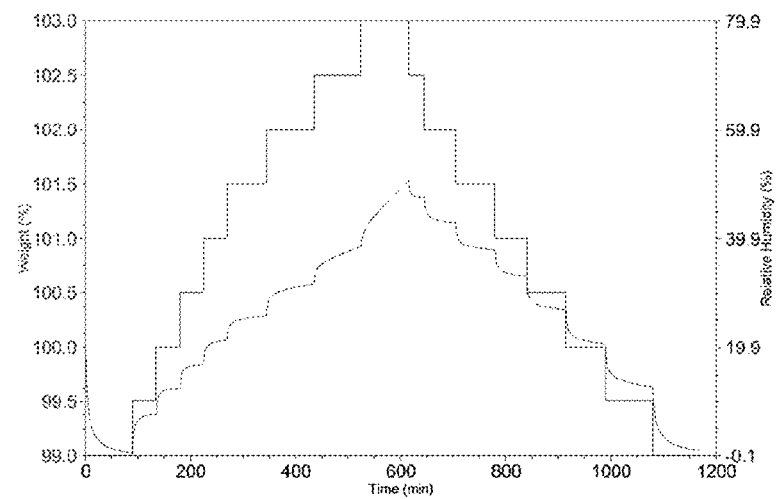
FIG. 4 is a DVS plot 1 of the sample of Example 1-1.
Figure 5:
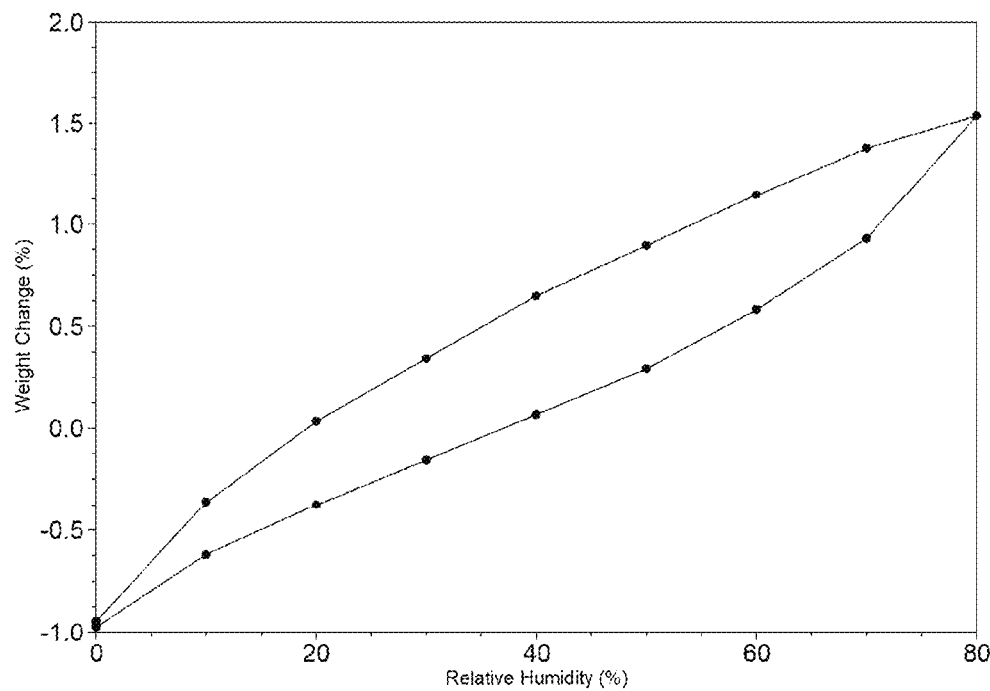
FIG. 5 is a DVS plot 2 of the sample of Example 1-1.

The DVS plot of sample 1-1 was measured at 25° C., with a weight gain of about 1.9% between 20% RH and 80% RH, as shown in FIG. 4-5.

Figure 6:
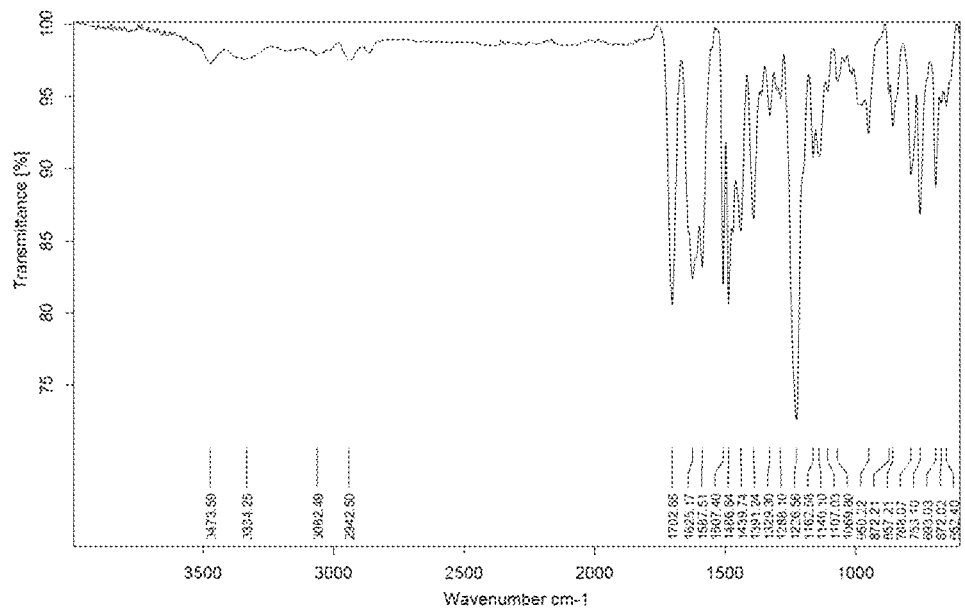
FIG. 6 is an FT-IR diagram of the sample of Example 1-1.

The FT-IR spectrum of sample 1-1 is shown in FIG. 6.

Example 1-2: Preparation of the Amorphous Form of Tolebrutinib

About 20 mg of tolebrutinib crude product was dissolved in 1.5 mL of toluene. After adding 4.0 mL of ether, solids precipitated. After stirring for two hours, and the mixture was centrifuged, and vacuum dried at room temperature for 24 hours to obtain amorphous sample 1-2.

Example 1-3: Preparation of the Amorphous Form of Tolebrutinib

About 30 mg of tolebrutinib crude product was dissolved in trifluoroethanol/water (0.3/0.4 ml) at 60° C. The solution was filtered, and then stirred at 4° C. for 2 days. After separation, the solid was dried to obtain amorphous product.

Example 1-4: Preparation of the Amorphous Form of Tolebrutinib

According to the method of Example 1-3, except for the crude product of tolebrutinib was dissolved in isopropyl acetate/water (0.1/0.3 ml), or tetrahydrofuran/water (0.1/0.4 ml), or 1,4-dioxane/water (0.05/0.2 ml), or acetonitrile/water (0.05/0.2 ml) or chloroform/water (0.4/0.2 ml). Keeping other conditions unchanged, amorphous products were obtained in all cases.

Example 2-1: Preparation of Tolebrutinib Form 1

About 20 mg of crude tolebrutinib was dissolved in 0.5 mL of ethyl acetate at room temperature. After stirring at room temperature for 1 day, the clear solution was cooled to 5° C. and stirred for 4 days. After adding 0.6 mL of purified water dropwise to the clear solution, solid precipitated. It was centrifuged, and the filtrations were vacuum dried at room temperature to obtain Tolebrutinib Form 1 sample 2-1.

The XRPD data of sample 2-1 is shown in the table below:

| 2θ | I % |
| --- | --- |
| 4.2 | 13.2 |
| 10.4 | 51.2 |
| 10.9 | 15.9 |
| 11.4 | 33.5 |
| 15.8 | 21.7 |
| 16.7 | 14.9 |
| 17.9 | 35.5 |
| 20.3 | 6.8 |
| 20.6 | 54.6 |
| 20.8 | 46.6 |
| 21.0 | 20.7 |

-continued

| 2θ | I % |
|---|---|
| 21.3 | 11.6 |
| 22.7 | 100.0 |
| 23.5 | 11.3 |
| 23.7 | 8.3 |
| 24.8 | 18.5 |
| 25.3 | 23.3 |
| 25.7 | 18.0 |
| 26.9 | 6.8 |
| 27.2 | 5.3 |
| 27.4 | 6.3 |
| 31.1 | 7.6 |
| 35.5 | 8.2 |

Figure 7:
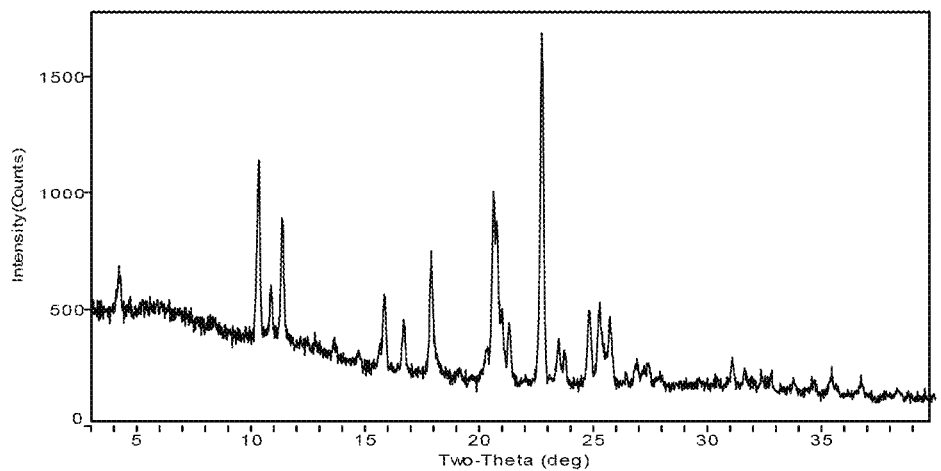
FIG. 7 is an XRPD pattern of the sample of Example 21-1 (Tolebrutinib Form 1).

The XRPD pattern of sample 2-1 is shown in FIG. 7.

Figure 8:
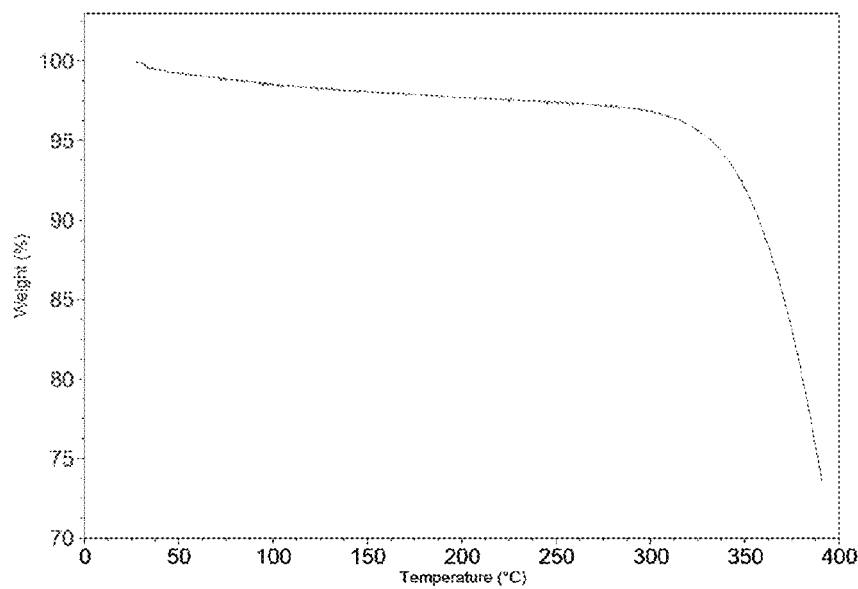
FIG. 8 is a TGA thermogram of the sample of Example 2-1.

The TGA of sample 2-1 was collected, indicating it to be anhydrous (with a weight loss of 1.4% before 100° C.), and showing a decomposition temperature of 346° C., as shown in FIG. 8.

Figure 9:
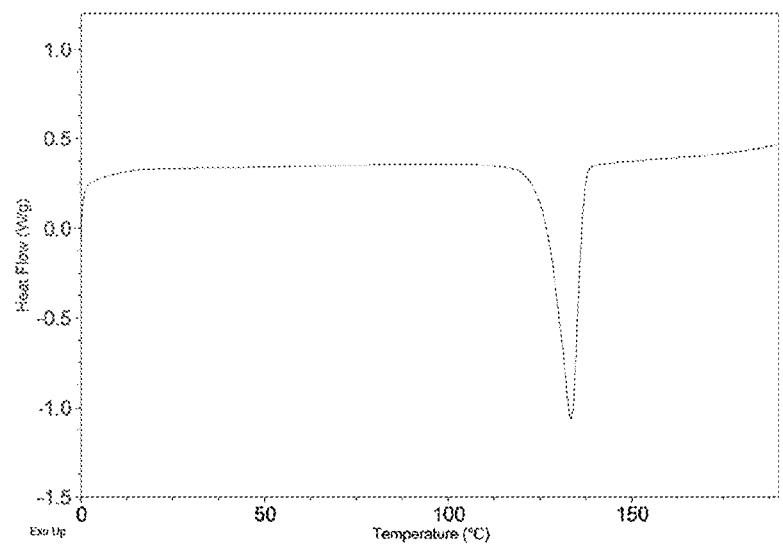
FIG. 9 is a DSC thermogram of the sample of Example 2-1.

The DSC data of sample 2-1 was collected, showing a melting (Onset) point of 126° C., i.e., an endothermic peak began to appear when heated to 126° C., and a peak value of 133° C., as shown in FIG. 9.

Figure 10:
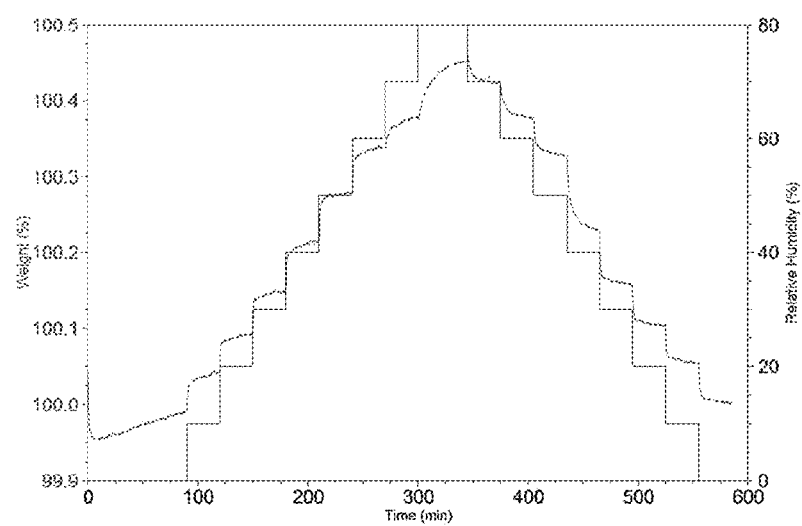
FIG. 10 is a DVS plot 1 of the sample of Example 2-1.
Figure 11:
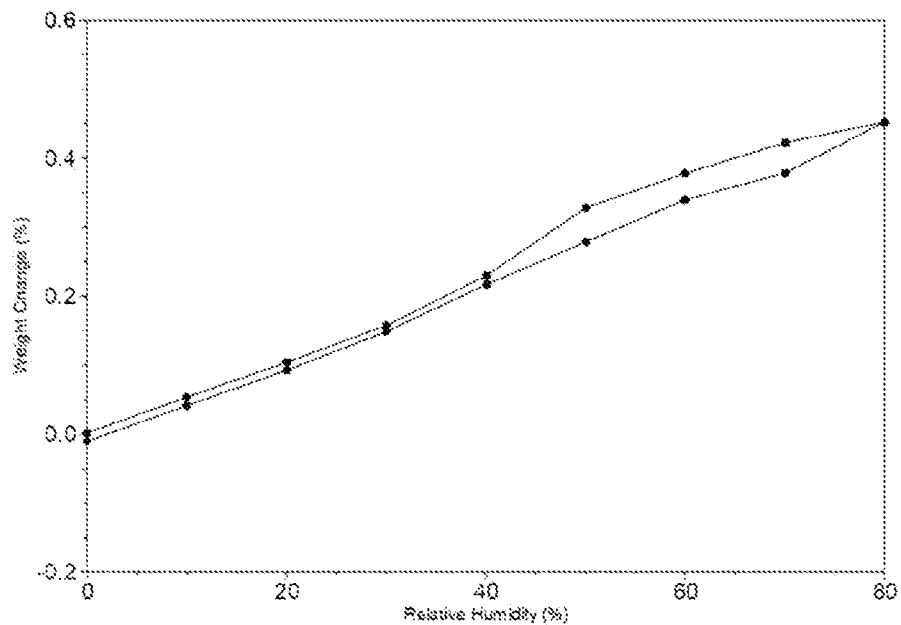
FIG. 11 is a DVS plot 2 of the sample of Example 2-1.

The DVS data of sample 2-1 was collected, with a weight gain of about 0.46% between 20% RH and 80% RH, as shown in FIG. 10-11.

Figure 12:
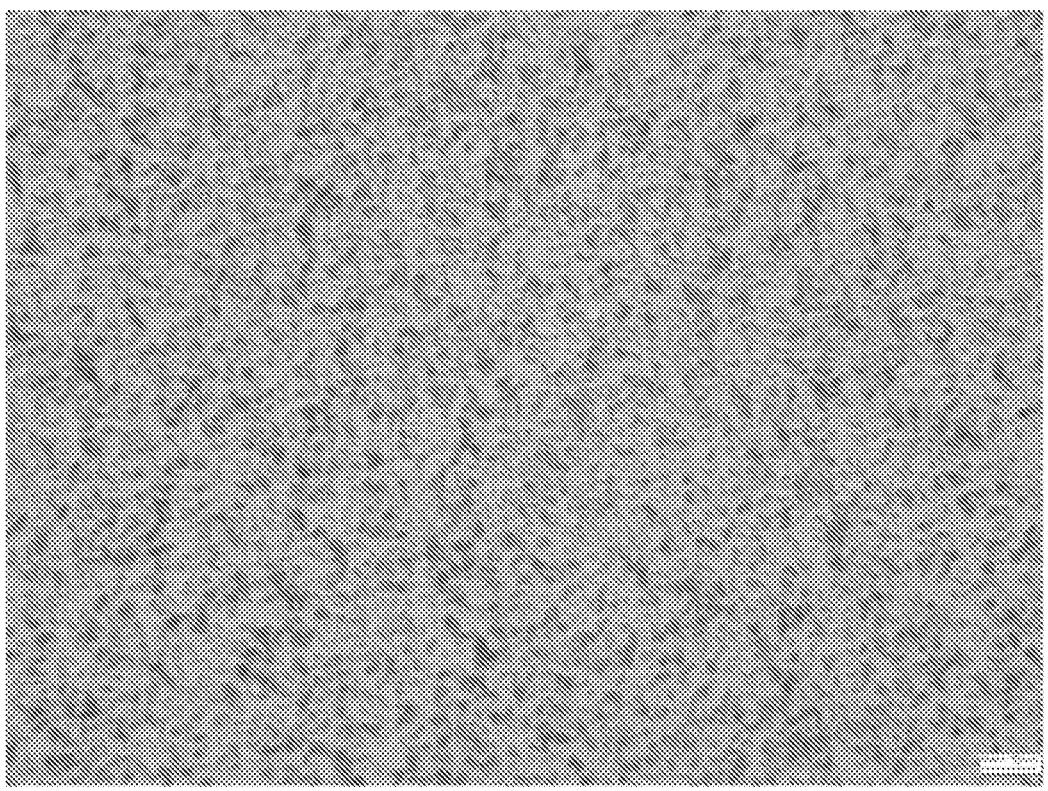
FIG. 12 is a PLM image of the sample of Example 2-1.

The PLM image of sample 2-1 was collected, with fine uniform particle size of ≤10 μm, as shown in FIG. 12.

Figure 13:
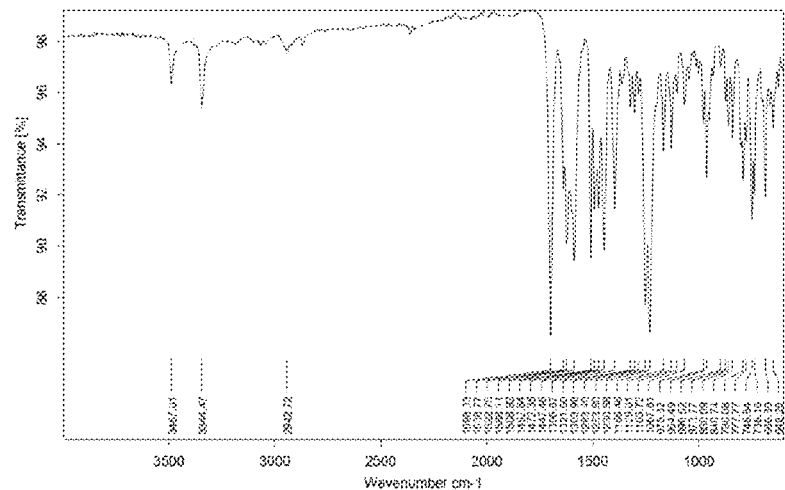
FIG. 13 is an FT-IR spectrum of the sample of Example 2-1.

The FT-IR spectrum of sample 2-1 is shown in FIG. 13.

Example 2-2: Preparation of Tolebrutinib Form 1

About 20 mg of the amorphous of tolebrutinib was dissolved in 0.5 mL acetone at room temperature, and the solution was filtered. It was volatilized at room temperature for 1 day to obtain Tolebrutinib Form 1.

Example 2-3: Preparation of Tolebrutinib Form 1

About 20 mg of the amorphous of tolebrutinib was dissolved in 0.5 mL tetrahydrofuran, and then filtered. Upon adding 1.2 mL of water, oily droplets were formed. After stirring at room temperature for one day, the mixture was transferred to 4° C. and stirred for 7 days. The resulting suspension was centrifuged, and after vacuum drying at room temperature overnight, tolebrutinib Form 1 sample was obtained.

Example 2-4: Preparation of Tolebrutinib Form 1

About 20 mg of the amorphous tolebrutinib was dissolved in 1.5 mL acetone at room temperature, filtered, and 4.0 mL of n-heptane was added to obtain a clear solution. The solution was stirred at room temperature for one day and then at 4° C. for stirring, after 7 days, the suspension was centrifuged, and vacuum dried overnight at room temperature, yielding Tolebrutinib Form 1.

Its XRPD data is shown in the table below:

| 2θ | I % |
|---|---|
| 4.2 | 13.6 |
| 10.4 | 50.8 |
| 10.9 | 16.1 |
| 11.4 | 33.8 |
| 15.9 | 22.0 |
| 16.7 | 14.8 |
| 17.9 | 35.1 |
| 20.4 | 8.0 |
| 20.6 | 54.6 |
| 20.8 | 47.5 |
| 21.0 | 19.8 |
| 21.3 | 13.2 |
| 22.8 | 100.0 |
| 23.5 | 12.2 |
| 23.8 | 9.2 |
| 24.8 | 19.6 |
| 25.3 | 23.4 |
| 25.7 | 18.3 |
| 26.9 | 6.9 |
| 27.4 | 6.4 |
| 31.1 | 8.0 |
| 35.5 | 8.5 |

Figure 30:
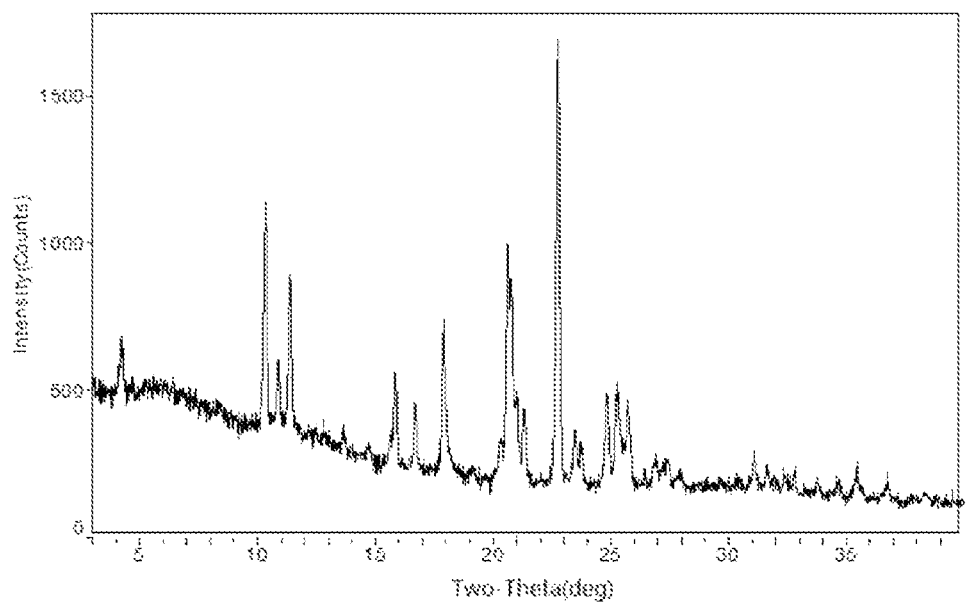
FIG. 30 is an XRPD pattern of the sample of Example 2-4 (tolebrutinib Form 1).

Its XRPD pattern is shown in FIG. 30.

Examples 2-5: Preparation of Tolebrutinib Form 1

About 20 mg of the amorphous tolebrutinib was dissolved in 0.5 mL acetone at room temperature, 4.0 mL of n-heptane was added to obtain a clear solution. The solution was stirred at room temperature for one day and then at 4° C. for stirring, after 7 days, the suspension was centrifuged, and vacuum dried overnight at room temperature, yielding Tolebrutinib Form 1.

Examples 2-6: Preparation of Tolebrutinib Form 1

About 50 mg of the amorphous tolebrutinib was dispersed in 1 mL of ethanol and was stirred at room temperature for 1 day. The solids were separated and dried in vacuum at room temperature to obtain Tolebrutinib Form 1.

Examples 2-7: Preparation of Tolebrutinib Form 1

About 50 mg of the amorphous tolebrutinib was dispersed in 1 mL of ethanol, and then stirred at room temperature for 2 days. The solids were separated and dried in vacuum at room temperature to obtain Tolebrutinib Form 1.

Examples 2-8: Preparation of Tolebrutinib Form 1

About 20 mg of the crude product of tolebrutinib was dissolved in 0.5 mL of ethanol at room temperature. After stirring at room temperature for 1 day, the clear solution was cooled to 5° C. and stirred for 4 days. After adding 4.0 mL of n-heptane drop wisely to the clear solution, solids precipitated. The solids were centrifuged and vacuum-dried at room temperature to obtain Tolebrutinib Form 1.

Example 3-1: Preparation of Tolebrutinib Form 2

Disperse about 20 mg of the amorphous of tolebrutinib in methyl tert-butyl ether (0.5 mL) to form a suspension, then slurred at 40° C. for 4 days, and then centrifuged. The solids were dried at room temperature overnight to obtain Form 2 sample 3-1.

The XRPD data of sample 3-1 is shown in the table below:

| 2θ | I % |
|---|---|
| 7.8 | 44.1 |
| 11.1 | 20.5 |
| 12.0 | 20.1 |
| 13.3 | 14.2 |
| 13.7 | 16.3 |
| 16.2 | 25.3 |
| 18.5 | 71.8 |
| 18.8 | 58.6 |
| 19.3 | 6.0 |
| 20.3 | 10.8 |
| 20.9 | 5.7 |
| 21.5 | 6.5 |
| 21.7 | 8.9 |
| 22.9 | 100.0 |
| 23.9 | 18.3 |
| 24.9 | 38.1 |
| 26.4 | 5.3 |
| 27.9 | 4.3 |
| 29.0 | 9.1 |
| 30.4 | 10.2 |

Figure 14:
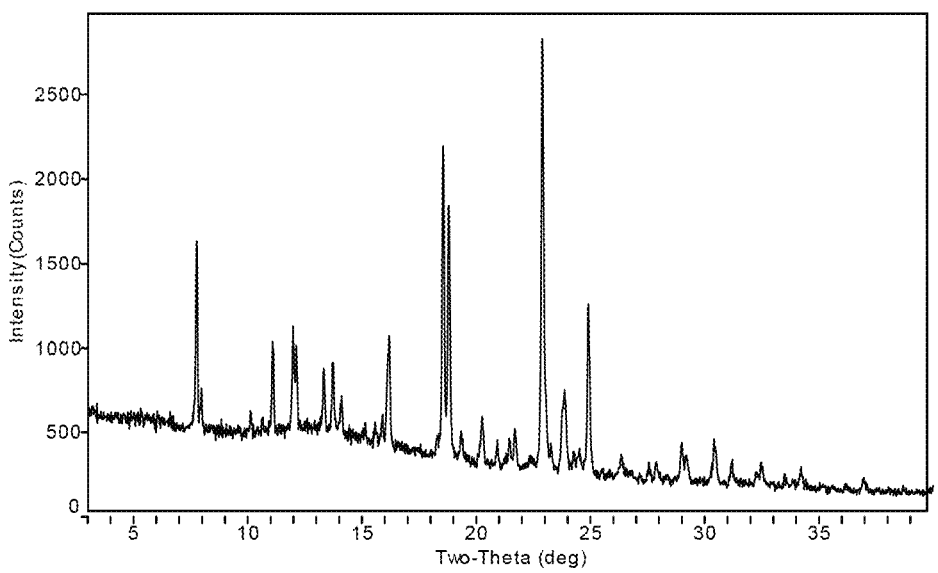
FIG. 14 is an XRPD pattern of the sample of Example 3-1 (Tolebrutinib Form 2).

The XRPD pattern of sample 3-1 is shown in FIG. 14.

Figure 15:
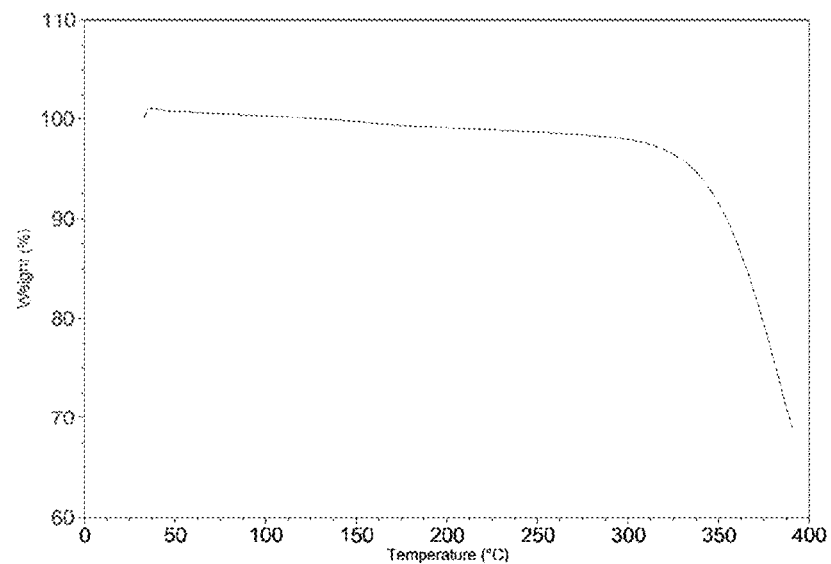
FIG. 15 is a TGA thermogram of the sample of Example 3-1.

The TGA data of sample 3-1 was collected, indicating it to be anhydrous, with a weight loss of 0.6% before 100° C., and showing a decomposition temperature of 342° C., as shown in FIG. 15.

Figure 16:
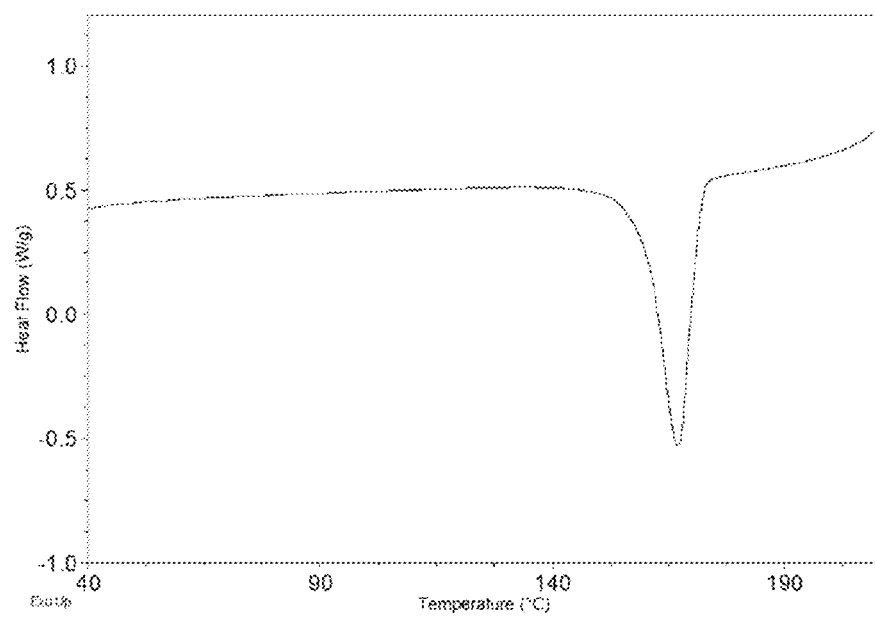
FIG. 16 is a DSC thermogram of the sample of Example 3-1.

The DSC data of sample 3-1 was collected, showing a melting (onset) point of 160° C., i.e., an endothermic peak began to appear when heated to 160° C., and a peak value of 167° C., as shown in FIG. 16.

Figure 17:
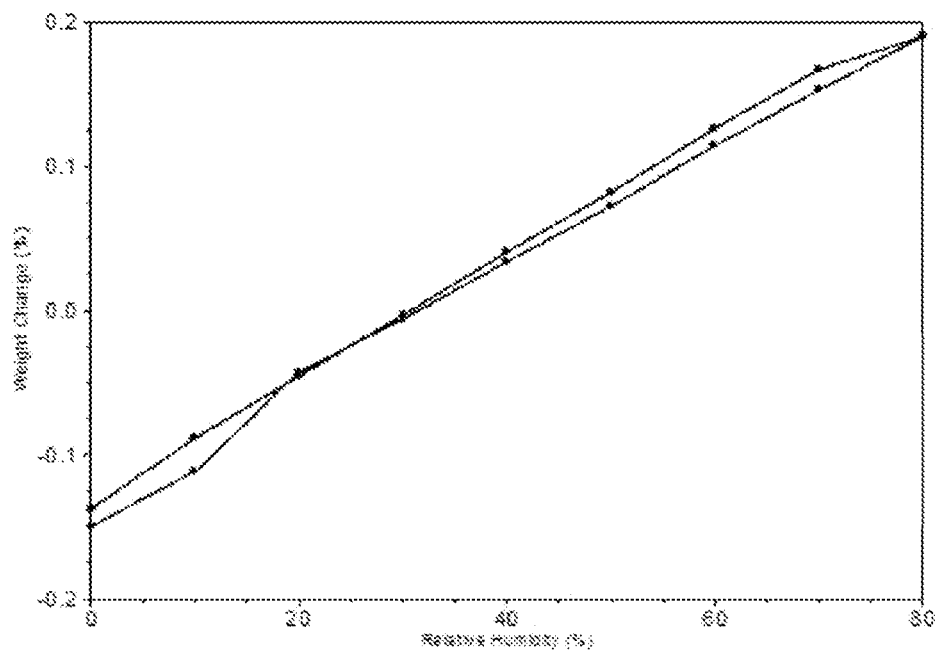
FIG. 17 is a DVS plot of the sample of Example 3-1.

The DVS data of sample 3-1 was collected, with a weight gain of about 0.34% between 0% RH and 80% RH, as shown in FIG. 17.

Figure 18:
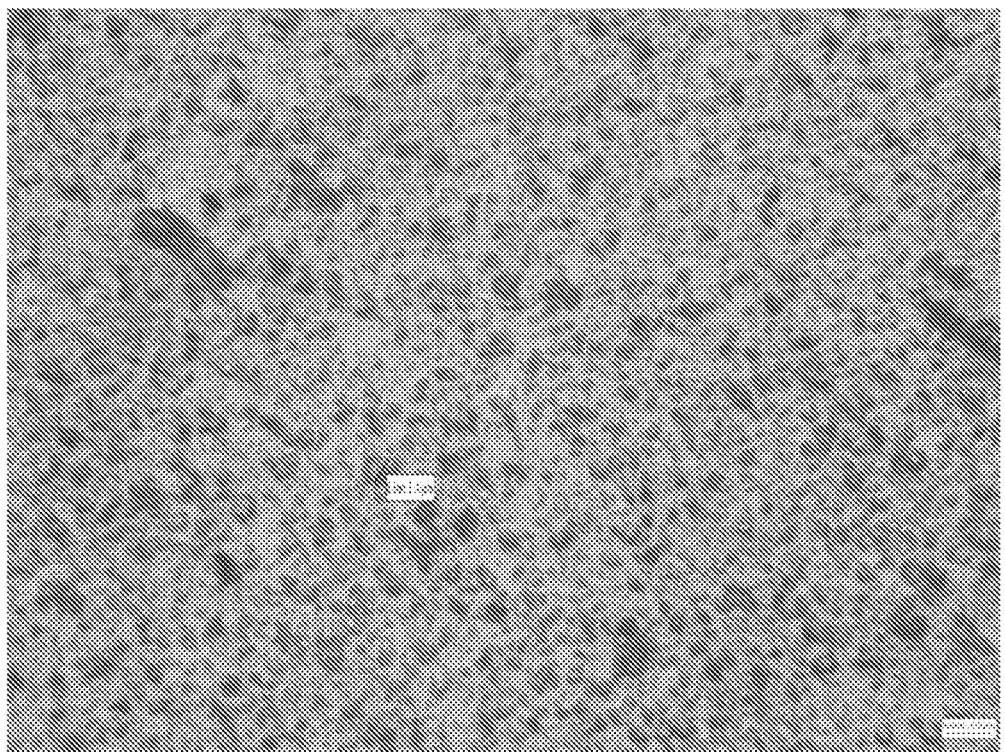
FIG. 18 is a PLM image of the sample of Example 3-1.

The PLM image of sample 3-1 was collected, with a fine uniform particle size of ≤10 μm, as shown in FIG. 18.

Figure 19:
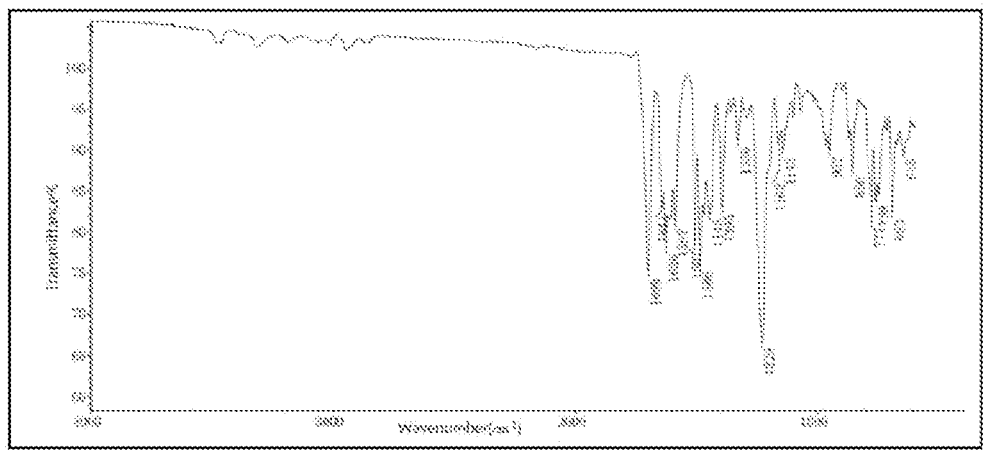
FIG. 19 is an FT-IR spectrum of the sample of Example 3-1.

The FT-IR spectrum of sample 3-1 is shown in FIG. 19.

Example 3-2: Preparation of Tolebrutinib Form 2

Dispersed about 20 mg of tolebrutinib crude product in butanone/water (0.1/0.5 mL) to form a suspension. The suspension was stirred at 70° C. for 3 days, centrifuged, and dried at room temperature overnight to obtain Form 2.

Its XRPD data is shown in the table below:

| 2θ | I % |
|---|---|
| 7.8 | 44.1 |
| 11.1 | 20.5 |
| 12.0 | 20.1 |
| 13.3 | 14.2 |
| 13.7 | 16.3 |
| 16.2 | 25.3 |
| 18.5 | 71.8 |
| 18.8 | 58.6 |
| 19.3 | 6.0 |
| 20.3 | 10.8 |
| 20.9 | 5.7 |
| 21.5 | 6.5 |
| 21.7 | 8.9 |
| 22.9 | 100.0 |
| 23.9 | 18.3 |
| 24.9 | 38.1 |
| 26.4 | 5.3 |
| 27.9 | 4.3 |
| 29.0 | 9.1 |
| 30.4 | 10.2 |

Figure 31:
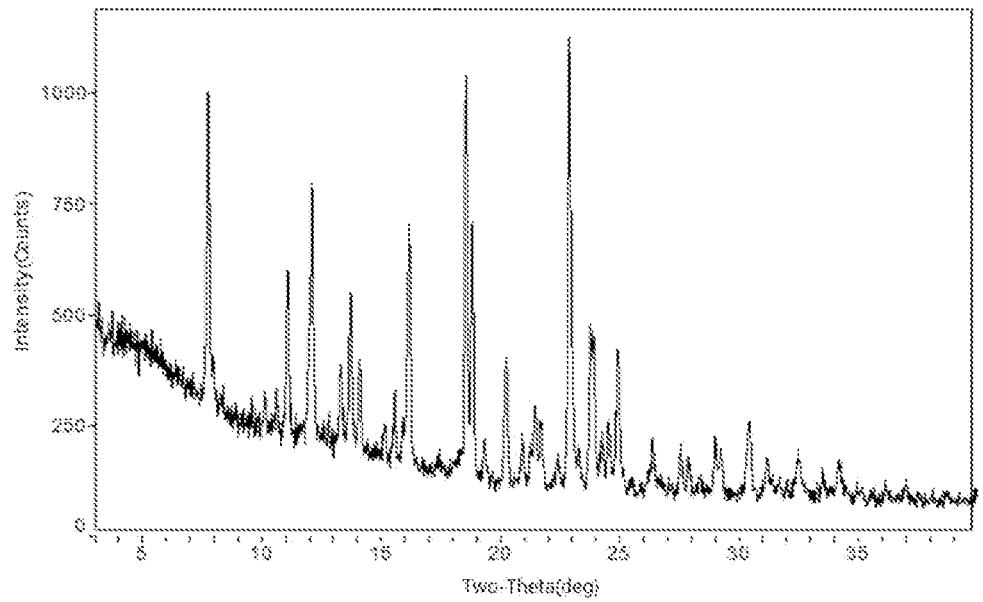
FIG. 31 is an XRPD pattern of the sample of Example 3-2 (the tolebrutinib Form 2).

Its XRPD pattern is shown in FIG. 31.

Example 3-3: Preparation of Tolebrutinib Form 2

Dispersed about 20 mg of the amorphous tolebrutinib in n-heptane (0.5 mL) to form a suspension. The suspension was stirred at a constant temperature of 50° C. for 5 days, centrifuged, and dried at room temperature overnight to obtain Form 2.

Example 3-4: Preparation of Tolebrutinib Form 2

Dispersed about 20 mg of the amorphous tolebrutinib in n-butyl acetate/dichloromethane (0.2/1.2 mL) to form a suspension, stirred at 40° C. for 5 days, centrifuged, and dried at room temperature overnight to obtain Form 2.

Example 3-5: Preparation of Tolebrutinib Form 2

About 20 mg of tolebrutinib crude product was placed in an acetonitrile atmosphere for 4 days, and then vacuum-dried at room temperature overnight to obtain Form 2.

Example 3-6: Preparation of Tolebrutinib Form 2

About 30 mg of tolebrutinib crude product was added to a toluene/methylcyclohexane system (0.55/0.2 mL), dissolved at 60° C., stirred at 5° C. for one day, and the clear solution was transferred to 40° C. after 2 days of open volatilization to obtain Form 2 sample 3-6.

Figure 32:
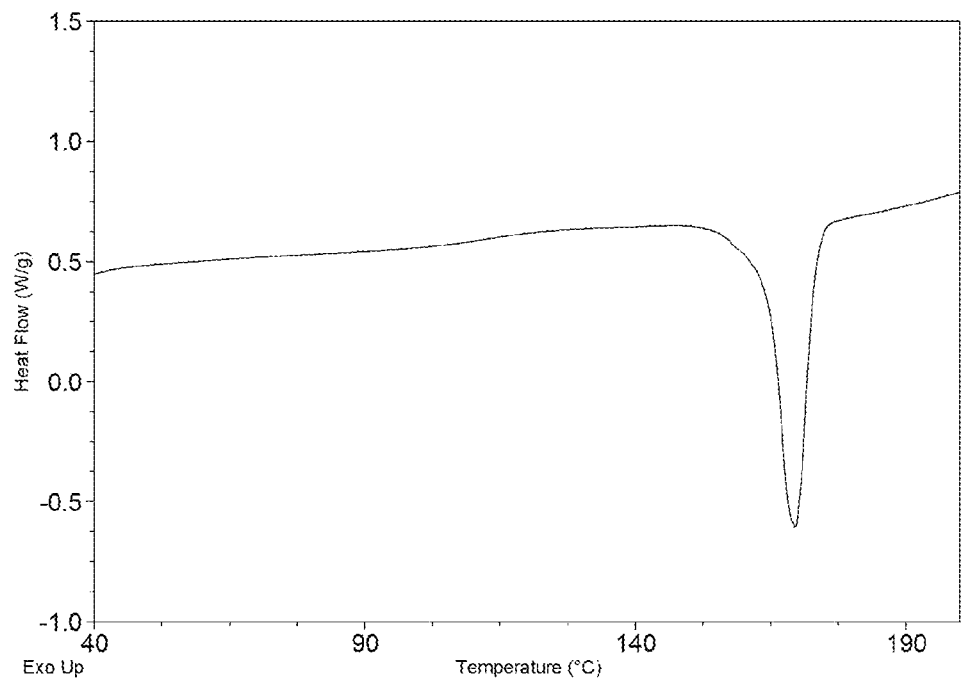
FIG. 32 is a DSC thermogram of the sample of Example 3-6.

The DSC data of sample 3-6 shows a melting (onset) point of 164° C., i.e., an endothermic peak began to appear when heated to 164° C. and a peak value of 170° C., as shown in FIG. 32.

Example 3-7: Preparation of Tolebrutinib Form 2

Following the method of Example 3-1, the crude product of tolebrutinib was dissolved in isopropyl ether (0.5 mL), or methanol/isopropyl ether (0.1/0.6 mL), or sec-butanol/n-heptane (0.6/0.6 mL), or 1,4-dioxane/isopropyl ether (0.2/0.6 mL), or methyl tert-butyl ether/n-butyl acetate (0.1/1.8 mL). Keeping the other conditions unchanged, Form 2 was obtained in all cases.

Example 4: Stability Study of the Amorphous, the Form 1 and Tolebrutinib Form 2

Figure 20:
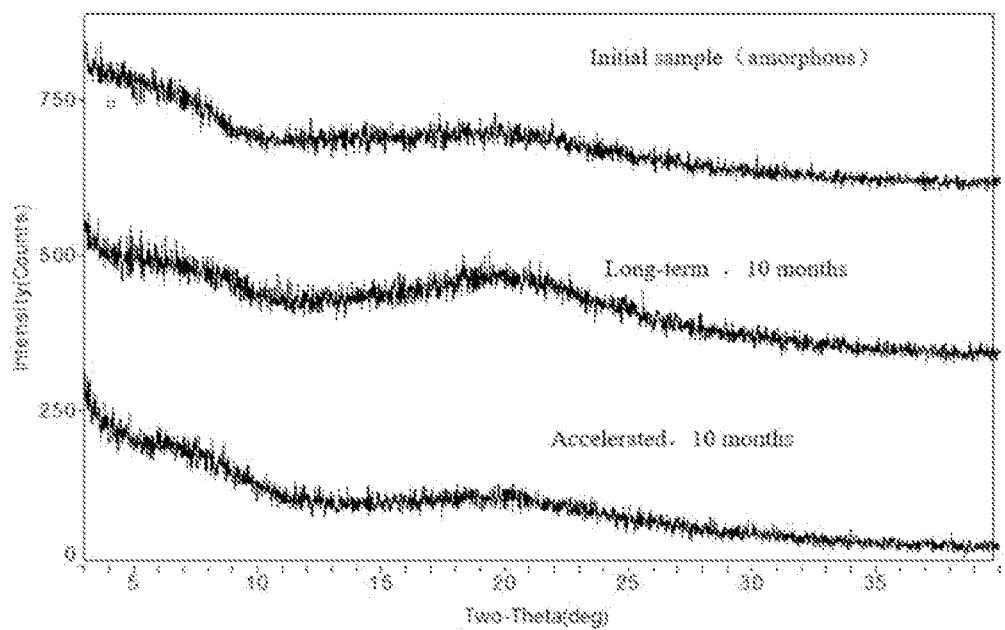
FIG. 20 shows an XRPD pattern overlay of the sample (amorphous form of tolebrutinib) of Example 1-1 before and after storing for 10 months under long-term (25° C./60% RH/open) and accelerated (40° C./75% RH/open) conditions.

An appropriate amount of amorphous form of tolebrutinib prepared in example 1-1 was subject to long-term (25° C./60% RH/open) and accelerated (40° C./75% RH/open) conditions. Regular testing using XRPD and HPLC was performed. The results were shown in Table 1 and FIG. 20.

TABLE 1

Stability of the amorphous form of tolebrutinib

| Initial sample | Initial purity | Placing conditions | Placing time | sample after placing | Purity after placing |
|---|---|---|---|---|---|
| Amorphous | 98.88% | 25° C./65% RH/open | 10 months | Amorphous | 98.87% |
| Amorphous | 98.88% | 40° C./75% RH/open | 10 months | Amorphous | 98.00% |

The experimental results show that: the amorphous tolebrutinib remains unchanged for 10 months under both long-term (25° C./60% RH/open) and accelerated (40° C./75% RH/open) conditions for 10 months, and its chemical purity remains essentially unchanged before and after storage. In addition, the amorphous tolebrutinib remains stable for at least 14 days under light (25° C./4500 lx/closed) and oxidation (in an atmosphere of carbamide peroxide) conditions, and its chemical purity remains essentially unchanged before and after storage.

Figure 21:
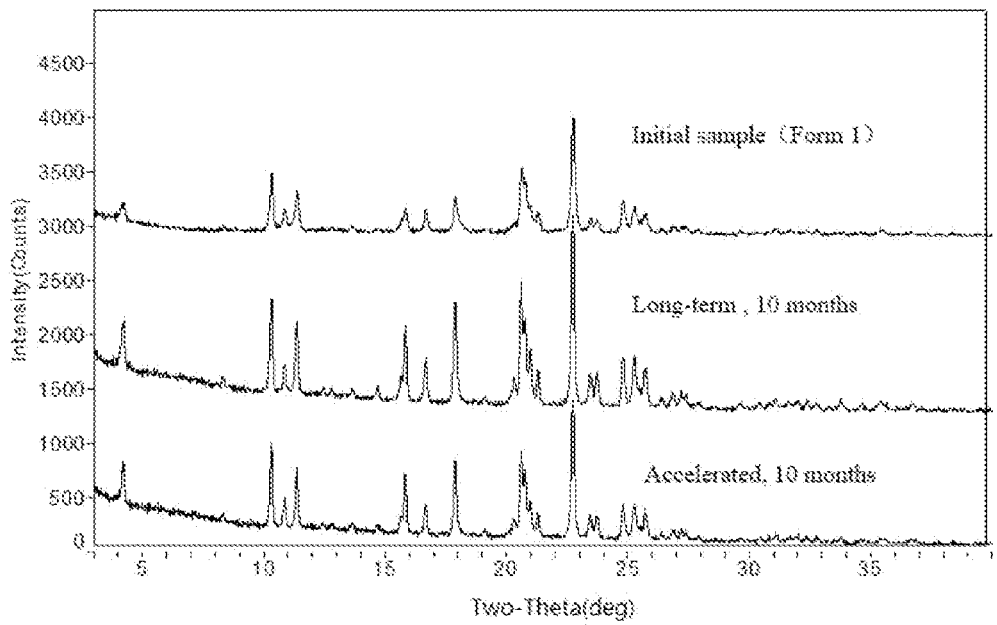
FIG. 21 shows an XRPD pattern overlay of the sample (Form 1) of Example 1-1 before and after storaging for 10 months under long-term (25° C./60% RH/open) and accelerated (40° C./75% RH/open) conditions.

An appropriate amount of Tolebrutinib Form 1 prepared in example 2-1 was subject to both long-term (25° C./60% RH/open) and accelerated (40° C./75% RH/open) stability conditions. Regular testing using XRPD and HPLC were performed. The results were shown in Table 2 and FIG. 21.

TABLE 2

Stability of tolebrutinib Form 1

| Initial sample | Initial purity | Placing conditions | Placing time | sample after placing | Purity after placing |
|---|---|---|---|---|---|
| Form 1 | 99.84% | 25° C./60% RH/open | 10 months | Form 1 | 99.77% |
| Form 1 | 99.84% | 40° C./75% RH/open | 10 months | Form 1 | 99.54% |

The experimental results show that Tolebrutinib Form 1 remains stable for at least 10 months under both long-term (25° C./60% RH/open) and accelerated (40° C./75% RH/open) conditions, and its chemical purity remains basically unchanged before and after storage. In addition, Form 1 remains stable for at least 14 days under both light (25° C./4500 lx/closed) and oxidation (in an atmosphere of carbamide peroxide) conditions, and its chemical purity remains basically unchanged before and after storage.

Figure 22:
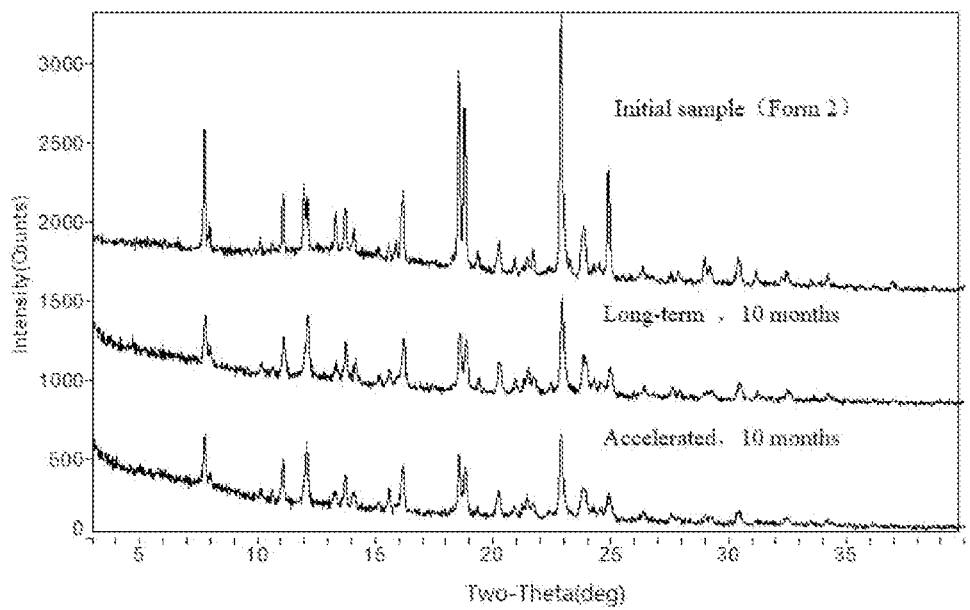
FIG. 22 shows an XRPD pattern overlay of the sample (Form 2) of Example 1-1 before and after storing for 10 months under long-term (25° C./60% RH/open) and accelerated (40° C./75% RH/open) conditions.

An appropriate amount of tolebrutinib Form 2 prepared in example 3-1 was subject to both long-term (25° C./60% RH/open) and accelerated (40° C./75% RH/open) conditions. Regular testing using XRPD and HPLC were performed. The results were shown in Table 3 and FIG. 22.

TABLE 3

Stability of tolebrutinib Form 2

| Initial sample | Initial purity | Placing conditions | Placing time | sample after placing | Purity after placing |
|---|---|---|---|---|---|
| Form 2 | 99.02% | 25° C./60% RH/open | 10 months | Form 2 | 98.87% |
| Form 2 | 99.02% | 40° C./75% RH/open | 10 months | Form 2 | 98.24% |

The experimental results show that tolebrutinib Form 2 remains stable for at least 10 months under both long-term (25° C./60% RH/open) and accelerated (40° C./75% RH/open) conditions, and its chemical purity of Form 2 remains basically unchanged before and after storage. In addition, Form 2 samples remains stable for at least 14 days under both light (25° C./4500 lx/closed) and oxidation (in an atmosphere of carbamide peroxide) conditions, and its chemical purity remains basically unchanged before and after storage.

Example 5: Solubility Studies of the Amorphous Form of Tolebrutinib, Tolebrutinib Form 1 and Tolebrutinib Form 2

The amorphous form of tolebrutinib, Form 1 and Form 2 samples of the present application were studied using pH 1.2 buffer solution (preparation: 375.90 mg potassium chloride solid and 1709.47 mg concentrated hydrochloric acid (37%) were added to a 100 mL volumetric flask, 80 mL of pure water was added, adjusted the pH to 1.2 with hydrochloric acid or potassium hydroxide, q.s. to volume) and pH 1.2 SGF (preparation: In 765 µL of concentrated hydrochloric acid (37%) added about 80 mL of water, 1 g of pepsin, 200 mg chlorinated sodium, shook, diluted with water to 100 mL) to form a supersaturated solution, and the dissolved content of the sample in the saturated solution was determined by high performance liquid chromatography (HPLC) at a fixed time point. The results are shown in Table 4:

TABLE 4

Solubility of amorphous form of tolebrutinib, Form 1 and Form 2 in pH 1.2 buffer and pH 1.2 SGF

| | Sample | Time | pH 1.2 buffer solution | pH 1.2 SGF |
|---|---|---|---|---|
| Solubility (mg/mL) | Amorphous | 2 hours | 29.08 | 36.76 |
| | Form 1 | 2 hours | 21.19 | 18.28 |
| | Form 2 | 2 hours | 21.44 | 32.45 |

As shown in Table 4, the solubility of amorphous form of tolebrutinib, Form 1 and Form 2 of the present application in pH 1.2 buffer and pH 1.2 SGF meets pharmaceutical requirements. The amorphous form, Form 1 and Form 2 of the present application have desirable solubility, all at approximately 20 mg/mL level. This characteristic is advantageous in achieving optimal drug bioavailability and efficacy, thereby meeting pharmaceutical requirements.

Example 6: Compressibility Studies of the Amorphous Form of Tolebrutinib, Form 1 and Form 2

The tablet compression was conducted using a Tianxiang rotary tablet press. A circular punch with a diameter of 7.5 mm (07.5 mm) was selected, a filling depth of 17.9 mm and a mean main pressure of 1.8 KN was used to form circular tablets. The tablets' radial breaking force (hardness, H) was measured using a tablet hardness tester. The tablets' diameter (D) and thickness (L) were measured using a vernier caliper. The tensile strength (T) of the powder was calculated using the formula T=2H/πDL*9.8. The results are shown in Table 5:

TABLE 5

Compressibility of amorphous form of tolebrutinib, Form 1 and Form 2

|  | amorphous | Form 1 | Form 2 |
|---|---|---|---|
| diameters (mm) | 7.49 | 7.51 | 7.51 |
| thicknesses (mm) | 4.15 | 4.18 | 4.18 |
| hardness (kg) | 7.18 | 6.40 | 8.31 |
| tensile strength (MPa) | 1.4 | 1.3 | 1.7 |

The results showed that, the amorphous form of tolebrutinib, Form 1 and Form 2 all had superior compressibility and met the pharmaceutical requirements.

Example 7: Preparation of Tablets

Following the formulation in Table 6, API, lactose hydrate, polyvinylpyrrolidone, hydroxypropyl cellulose, microcrystalline cellulose and magnesium stearate were mixed and compressed to obtain a tablet core. Subsequently, the tablet cores are coated with a solution/suspension for film coating, resulting in the preparation of the tablets.

TABLE 6

Tablet formulations

|  | Component | Per tablet (mg) | Per tablet (mg) |
|---|---|---|---|
| Tablet Core: | API | 60 | 120 |
|  | Microcrystalline cellulose | 23.5 | 42 |
|  | Lactose hydrate | 90 | 185 |
|  | Polyvinylpyrrolidone K30 | 12.5 | 22 |
|  | Hydroxypropyl cellulose | 12.5 | 28 |
|  | Sodium starch glycolate | 1.5 | 3 |
|  | Total mixed sample (Tablet Core Weight) | 200 | 400 |
| Film Coating | Hydroxypropyl methylcellulose | 3.5 | 7.0 |
|  | Polyethylene glycol 6000 | 0.8 | 1.6 |
|  | Talc | 1.3 | 2.6 |
|  | Iron oxide (yellow) | 0.8 | 1.6 |
|  | Titanium dioxide | 0.8 | 1.6 |

Note:
The APIs are amorphous, Form 1 and Form 2, respectively.

Figure 23:
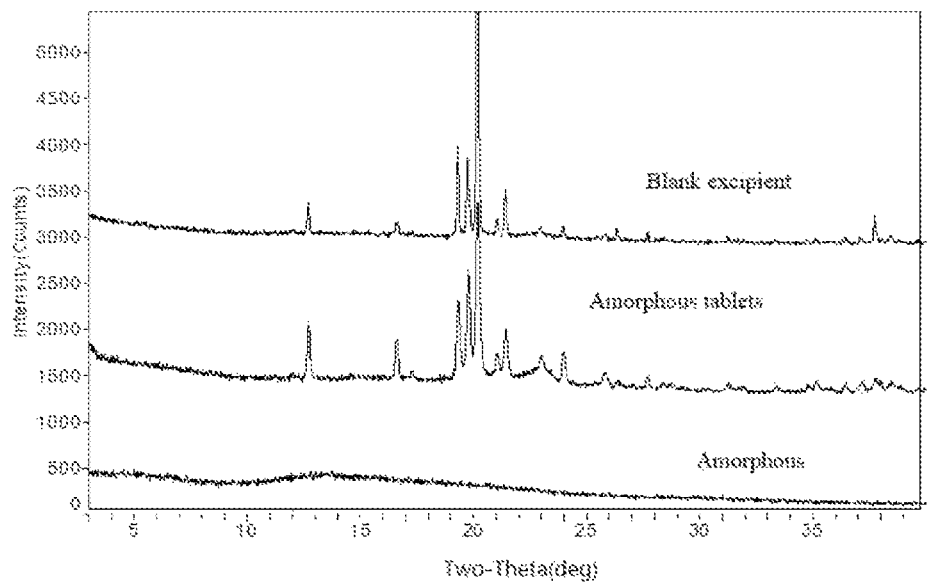
FIG. 23 shows an XRPD pattern overlay of the sample (amorphous form of tolebrutinib) of Example 1-1 before and after the formulation.
Figure 24:
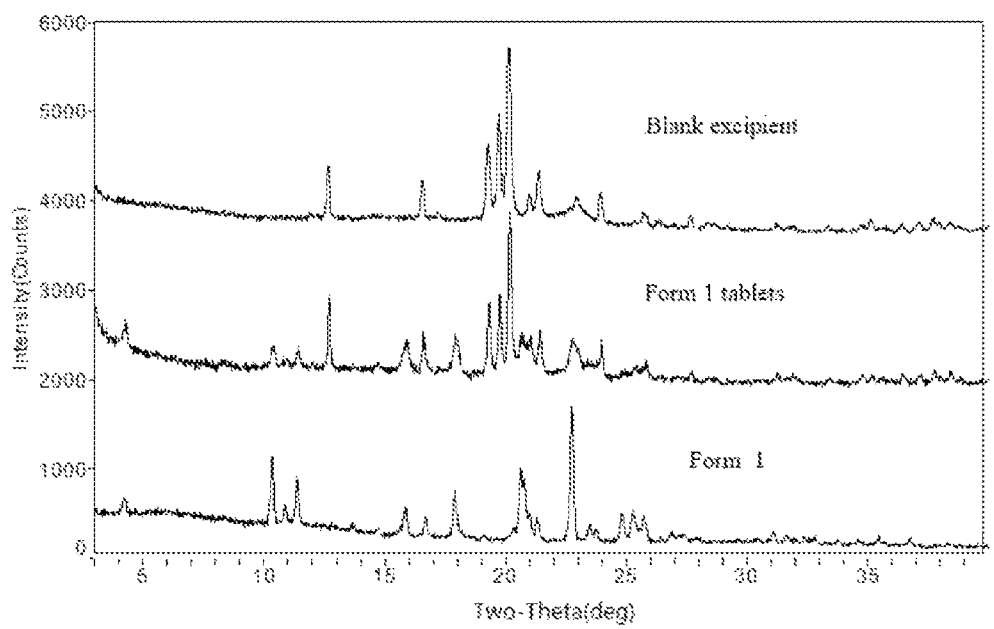
FIG. 24 shows an XRPD pattern overlay of the sample (Form 1) of Example 2-1 before and after the formulation.
Figure 25:
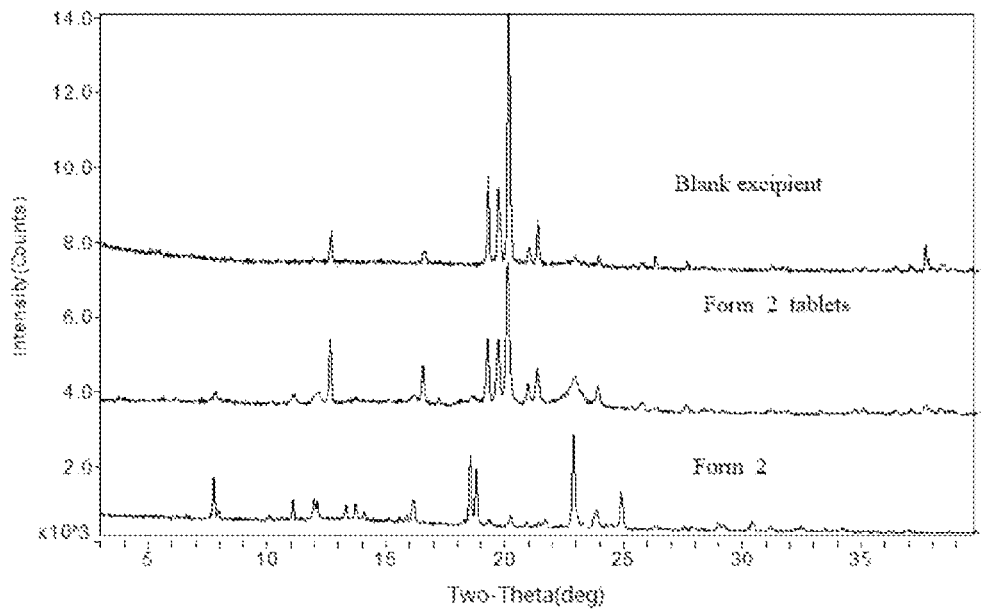
FIG. 25 shows an XRPD pattern overlay of the sample (Form 2) of Example 3-1 before and after the formulation.

The solid forms of the amorphous form of tolebrutinib, Form 1 and Form 2 remained unchanged before and after the tableting process, and the XRPD comparison plots are shown in FIG. 23, FIG. 24 and FIG. 25, respectively.

Example 8: Preparation of Capsules

The capsules were prepared by sieving and mixing the components in hard gelatin capsules according to the formulation in Table 7.

TABLE 7

Capsule formulation

| Component | Per capsule (mg) | Per capsule (mg) |
|---|---|---|
| API | 60 | 120 |
| Lactose | 50 | 100 |
| Sodium starch glycolate | 0.8 | 1.5 |

Note:
The APIs are amorphous, Form 1 and Form 2, respectively.

Figure 26:
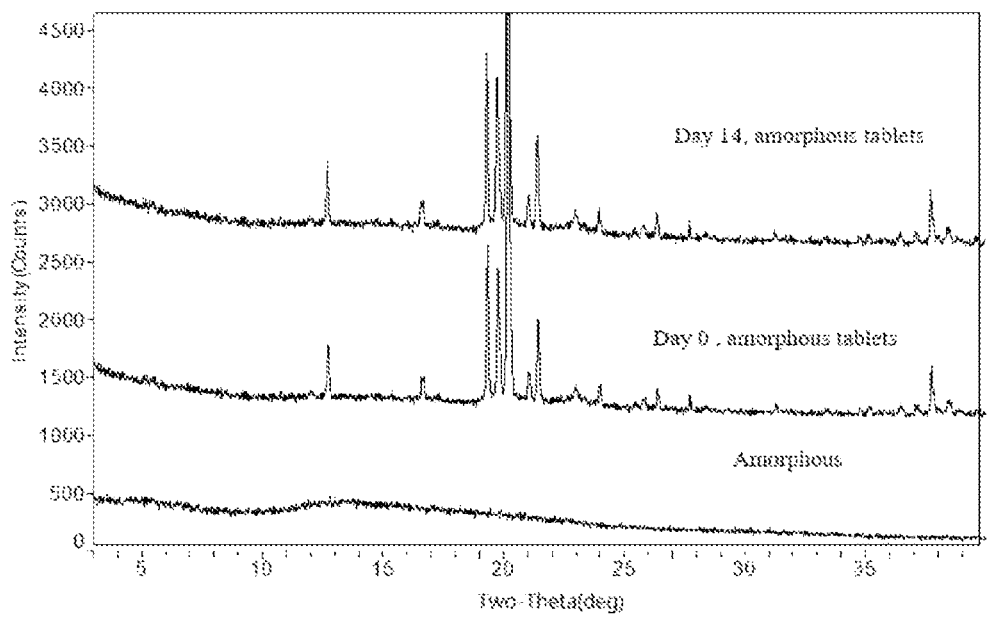
FIG. 26 shows an XRPD pattern overlay of the tablet stability sample (amorphous form of tolebrutinib) of Example 1-1.
Figure 27:
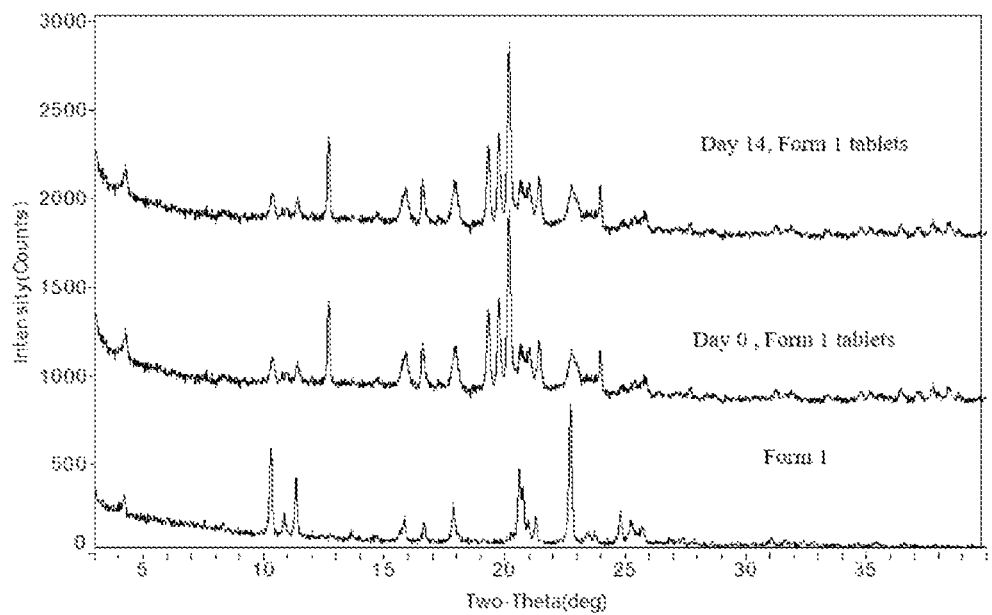
FIG. 27 shows an XRPD pattern overlay of the tablet stability sample (Form 1) of Example 2-1.
Figure 28:
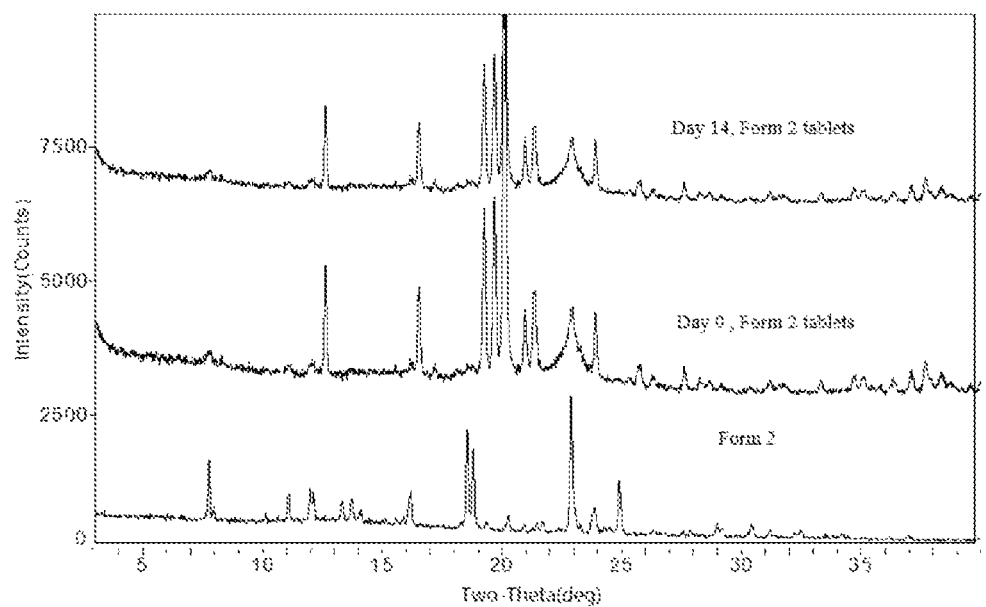
FIG. 28 shows an XRPD pattern overlay of the tablet stability sample (Form 2) of Example 3-1.
Figure 29:
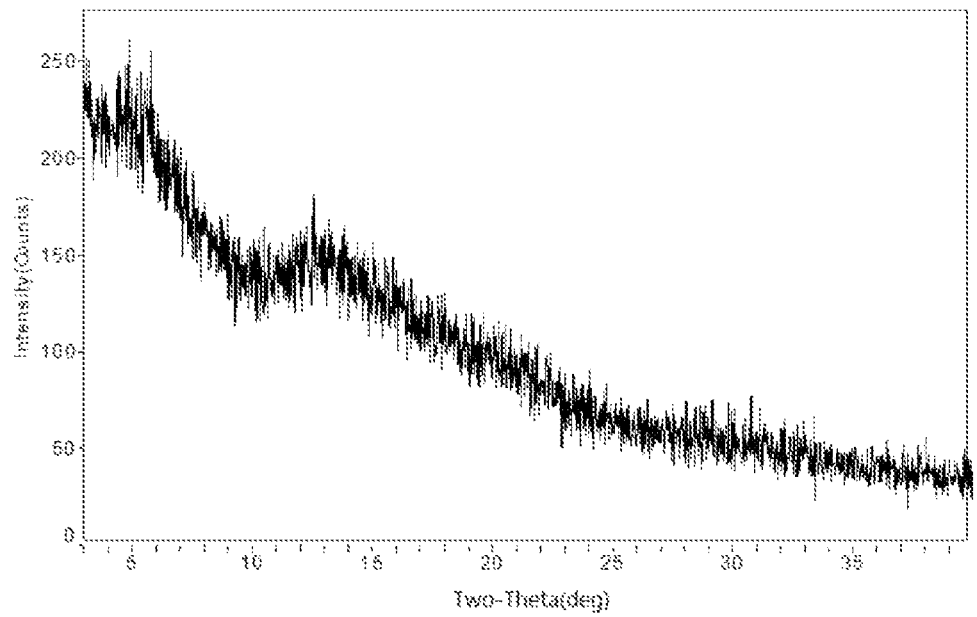
FIG. 29 is an XRPD pattern of the sample of Example 1-2 (the amorphous form of tolebrutinib)

Example 9: Stability of the Amorphous Form of Tolebrutinib, Form 1 and Form 2 in Tablets The prepared amorphous tablets, Form 1 tablets and Form 2 tablets were individually placed at 25° C./60% RH for 14 days. XRPD tests were performed before and after storage. The XRPD comparison plots before and after storage are shown in FIG. 26, FIG. 27 and shown in FIG. 28, respectively.

The results showed that the amorphous tablets, Form 1 tablets and Form 2 tablets remain stable for at least 14 days under the 25° C./60% RH condition.

The above examples are the preferred embodiments of the application, but the implementation of the application is not limited to the above examples. Any modifications, alterations, substitutions, combinations, simplifications, or changes made within the scope of the spirit and essence of the present application, which do not depart from the scope of the present application, are considered to be equivalent alternatives and are encompassed within the scope of protection of the present application.

The invention claimed is:

1. Tolebrutinib Form 2 of the following formula,

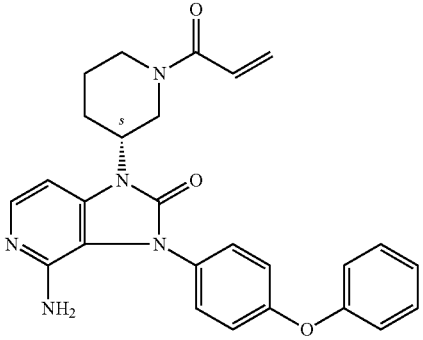 [SMILES: C=CC(=O)N1CCC[C@@H](n2c(=O)n(-c3ccc(Oc4ccccc4)cc3)c3c(N)nccc32)C1]

wherein the XRPD pattern of Form 2 comprises at least four characteristic peaks at 2θ values of 7.8°±0.2°, 12.0°±0.2°, 18.5°±0.2°, 18.8°±0.2° and 22.9°±0.2°.

2. The tolebrutinib Form 2 according to claim 1, wherein the XRPD pattern of Form 2 also comprises one or two or more characteristic peaks at 2θ values of 11.1°±0.2°, 13.7°±0.2°, 16.2°±0.2°, 23.9°±0.2° and 24.9°±0.2°.

3. The tolebrutinib Form 2 according to claim 1, wherein the XRPD pattern of Form 2 also comprises one or two or more characteristic peaks at 2θ values of 13.3°±0.2°, 14.1°±0.2°, 20.3°±0.2° and 21.7°±0.2°.

4. The tolebrutinib Form 2 according to claim 1, wherein the XRPD pattern of Form 2 comprises characteristic peaks at the following 2θ values:

| 2θ ± 0.2° |
|---|
| 7.8 |
| 11.1 |
| 12.0 |
| 13.3 |
| 13.7 |
| 16.2 |
| 18.5 |
| 18.8 |
| 19.3 |
| 20.3 |
| 20.9 |

-continued

| 2θ ± 0.2° |
|---|
| 21.5 |
| 21.7 |
| 22.9 |
| 23.9 |
| 24.9 |
| 26.4 |
| 27.9 |
| 29.0 |
| 30.4 |

5. The tolebrutinib Form 2 according to claim 1, wherein the XRPD pattern of Form 2 is substantially as depicted in FIG. 14.

6. The tolebrutinib Form 2 according to claim 1, wherein the DSC thermogram of Form 2 begins to show an endothermic peak at about 160-164° C.

7. The tolebrutinib Form 2 according to claim 1, wherein the FT-IR spectrum of Form 2 comprises bands at wave numbers of 1699±2 cm$^{-1}$, 1229±2 cm$^{-1}$, 1486 cm$^{-1}$, and 1507±2 cm$^{-1}$.

8. Tolebrutinib Form 1 of the following formula,

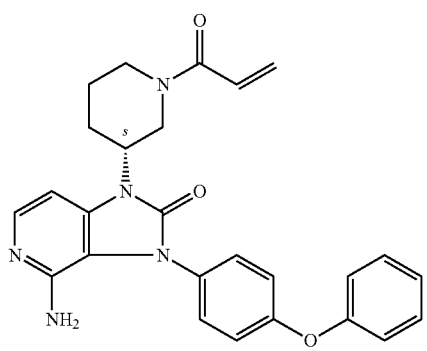 [SMILES: C=CC(=O)N1CCC[C@@H](n2c(=O)n(-c3ccc(Oc4ccccc4)cc3)c3c(N)nccc32)C1]

wherein the XRPD pattern of the Form 1 comprises at least four characteristic peaks at 2θ values of 10.4°±0.2°, 11.4°±0.2°, 20.6°±0.2°, 16.7°±0.2° and 22.7°±0.2°.

9. Tolebrutinib Form 1 according to claim 8, wherein the XRPD pattern of the Form 1 also comprises one or two or more characteristic peaks at 2θ values of 4.2°±0.2°, 15.8°±0.2°, 17.9°±0.2°, 20.8°±0.2° and 24.8°±0.2°.

10. Tolebrutinib Form 1 according to claim 8, wherein the XRPD pattern also comprises one or two or more characteristic peaks at 2θ values of 10.9°±0.2°, 121.3°±0.2°, 23.5°±0.2°, 25.3°±0.2° and 25.7°±0.2°.

11. Tolebrutinib Form 1 according to claim 8, wherein the XRPD pattern of the Font' 1 comprises characteristic peaks at the following 2θ values:

| 2θ ± 0.2° |
|---|
| 4.2 |
| 10.4 |
| 10.9 |
| 11.4 |
| 15.8 |
| 16.7 |
| 17.9 |
| 20.3 |
| 20.6 |
| 20.8 |
| 21.0 |

-continued

| 2θ ± 0.2° |
|---|
| 21.3 |
| 22.7 |
| 23.5 |
| 23.7 |
| 24.8 |
| 25.3 |
| 25.7 |
| 26.9 |
| 27.2 |
| 27.4 |
| 31.1 |
| 35.5 |

12. Tolebrutinib Form 1 according to claim 8, wherein the XRPD pattern of the Form 1 is substantially as depicted in FIG. 7.

13. Tolebrutinib Form 1 according to claim 8, wherein the DSC thermogram of Form 1 begins to show an endothermic peak at about 126° C.

14. Tolebrutinib Form 1 according to claim 8, wherein the FT-IR spectrum of Form 1 comprises bands at wave numbers of 840.7±2 cm$^{-1}$, 978.3±2 cm$^{-1}$, 1472.3±2 cm$^{-1}$, 1492.5±2 cm$^{-1}$.

15. Amorphous form of tolebrutinib of the following formula,

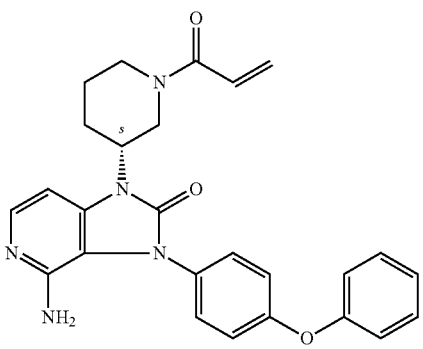 [SMILES: C=CC(=O)N1CCC[C@@H](n2c(=O)n(-c3ccc(Oc4ccccc4)cc3)c3c(N)nccc32)C1]

wherein the XRPD pattern of the amorphous form has no diffraction peaks at 2θ value within the range of 3-40°.

16. The amorphous of tolebrutinib according to claim 15, wherein the XRPD pattern of the amorphous form has a broad hump at 2θ values within the range of 10-40°.

17. The amorphous form of tolebrutinib according to claim 15, wherein the XRPD pattern of the amorphous is substantially as depicted in FIG. 1.

18. The amorphous form of tolebrutinib according to claim 15, wherein the FT-IR spectrum of the amorphous form comprises bands at wave numbers of 1703±2 cm$^{-1}$, 1440±2 cm$^{-1}$, 788±2 cm$^{-1}$, and 753±2 cm$^{-1}$.

19. A pharmaceutical composition comprising one or more of tolebrutinib Form 2 according to claim 1, and at least one pharmaceutically acceptable carrier.

20. A method of treating multiple sclerosis, comprising administering to a patient in need thereof a therapeutically effective amount of one or more of tolebrutinib Form 2 according to claim 1, or a pharmaceutical composition thereof.

21. A pharmaceutical composition comprising one or more of tolebrutinib Form 1 according to claim 8, and at least one pharmaceutically acceptable carrier.

22. A method of treating multiple sclerosis, comprising administering to a patient in need thereof a therapeutically effective amount of one or more of tolebrutinib Form 1 according to claim 8, or a pharmaceutical composition thereof.

23. A pharmaceutical composition comprising one or more of amorphous form of tolebrutinib according to claim 15, and at least one pharmaceutically acceptable carrier.

24. A method of treating multiple sclerosis, comprising administering to a patient in need thereof a therapeutically effective amount of one or more of amorphous form of tolebrutinib according to claim 15, or a pharmaceutical composition thereof.

\* \* \* \* \*